US011482322B1

(12) United States Patent
Bhansali et al.

(10) Patent No.: US 11,482,322 B1
(45) Date of Patent: Oct. 25, 2022

(54) PATIENT TRACKERBOARD TOOL AND INTERFACE

(71) Applicant: MedAmerica Data Services, LLC, Emeryville, CA (US)

(72) Inventors: Vivek Bhansali, San Jose, CA (US); Jimmy Guillén, Oakland, CA (US); Travis Payne, San Francisco, CA (US); Jenny Hyun, San Jose, CA (US); Dipti Patel-Misra, Alamo, CA (US); Joshua Tamayo-Sarver, Los Gatos, CA (US)

(73) Assignee: MEDAMERICA DATA SERVICES, LLC, Emeryville, CA (US)

( * ) Notice: Subject to any disclaimer, the term of this patent is extended or adjusted under 35 U.S.C. 154(b) by 67 days.

(21) Appl. No.: 16/378,439

(22) Filed: Apr. 8, 2019

Related U.S. Application Data

(60) Provisional application No. 62/701,243, filed on Jul. 20, 2018.

(51) Int. Cl.
*G16H 40/20* (2018.01)
*G16H 30/20* (2018.01)
*G16H 10/60* (2018.01)

(52) U.S. Cl.
CPC ............. *G16H 40/20* (2018.01); *G16H 10/60* (2018.01); *G16H 30/20* (2018.01)

(58) Field of Classification Search
CPC ........ G16H 30/20; G16H 50/50; G16H 40/40; G16H 10/40; G16H 10/60; G16H 40/20
USPC .......................................................... 705/3
See application file for complete search history.

(56) References Cited

U.S. PATENT DOCUMENTS

| 8,417,533 | B2 | 4/2013 | Clawson |
| 9,092,964 | B1 | 7/2015 | Chan et al. |
| 9,177,106 | B2 | 11/2015 | Smith et al. |
| 2004/0078236 | A1 | 4/2004 | Stoodley et al. |
| 2004/0087864 | A1 | 5/2004 | Grouse |

(Continued)

FOREIGN PATENT DOCUMENTS

| WO | WO-2014042942 A1 * | 3/2014 | ............. G06Q 50/24 |
| WO | WO-2014100736 A2 * | 6/2014 | ............. G16H 20/10 |

(Continued)

OTHER PUBLICATIONS

Chatterjee, Ayan et al.; HL7 FHIR with SNOMED-CT to Achieve Semantic and Structural Interoperability in Personal Health Data: A Proof-of-Concept Study; Sensors 22.10: 3756. MDPI AG. (2022) (Year: 2022).*

(Continued)

*Primary Examiner* — Hiep V Nguyen
(74) *Attorney, Agent, or Firm* — Mauriel Kapouytian Woods LLP; Elaine K. Lee; Michael Mauriel

(57) ABSTRACT

The present invention provides systems and methods for use with electronic records, such as Electronic Medical Records (EMRs). A parser engine may receive a stream of Health Level 7 (HL7) messages containing EMR data and, using parsing logic, parse the HL7 messages to identify and extract specified EMR data therefrom. The extracted EMR data may be combined with analytic results data and presented via a trackerboard with refresh and writeback capability, to a medical professional or medical staff member, in real time or near real time relative to entry of the EMR data into an EMR system.

20 Claims, 12 Drawing Sheets

(56) References Cited

U.S. PATENT DOCUMENTS

| | | | |
|---|---|---|---|
| 2007/0168223 A1* | 7/2007 | Fors | G16H 40/20 |
| | | | 705/2 |
| 2008/0154642 A1 | 6/2008 | Marble et al. | |
| 2008/0255885 A1 | 10/2008 | Eisenberger et al. | |
| 2012/0029932 A1 | 2/2012 | Stein et al. | |
| 2012/0215560 A1 | 8/2012 | Ofek et al. | |
| 2012/0323588 A1 | 12/2012 | Kelly et al. | |
| 2014/0236626 A1 | 8/2014 | Reddy Bynagari | |
| 2014/0297302 A1 | 10/2014 | Vanier et al. | |
| 2015/0213224 A1* | 7/2015 | Amarasingham | G16H 50/30 |
| | | | 705/2 |
| 2015/0287317 A1* | 10/2015 | Chan | G08B 25/016 |
| | | | 340/539.12 |
| 2015/0339791 A1 | 11/2015 | Tetteh | |
| 2016/0063209 A1 | 3/2016 | Malaviya | |
| 2016/0364544 A1 | 12/2016 | Das et al. | |
| 2017/0006135 A1* | 1/2017 | Siebel | H04L 69/40 |
| 2017/0061093 A1 | 3/2017 | Amarasingham et al. | |
| 2017/0091388 A1 | 3/2017 | Zolla et al. | |
| 2017/0277732 A1 | 9/2017 | Dwire et al. | |

FOREIGN PATENT DOCUMENTS

| | | | | |
|---|---|---|---|---|
| WO | 2017/091603 A1 | 6/2017 | | |
| WO | WO-2017091603 A1 * | 6/2017 | | G16H 10/60 |

OTHER PUBLICATIONS

Guillen, J., et al., U.S. Appl. No. 16/378,542, entitled Patent Callback Tools and Interface, filed Apr. 8, 2019.

Sutton, N., et al., U.S. Appl. No. 16/378,460, entitled Method and System for Cardiac Risk Assessment of a Patient Using Historical and Real-Time Data, filed Apr. 8, 2019.

Bhansali, V., et al., U.S. Appl. No. 16/297,456, entitled Real Time Parser for Use With Electronic Medical Records, filed Mar. 8, 2019.

Hsia, R.Y., et al., A National Study of the Prevalence of Life-Threatening Diagnoses in Patients with Chest Pain, Jul. 2016, pp. 1029-1032, vol. 176—No. 7, JAMA Internal Medicine.

Antman, E.M., et al., The TIMI Risk Score for Unstable Angina/Non-ST Elevation MI, A Method for Prognostication and Therapeutic Decision Making, American Medical Association, Aug. 16, 2000, pp. 835-842, vol. 284—No. 7, JAMA.

Lagerqvist, B., et al., FRISC score for selection of patients for an early invasive treatment stiategy in unstable coronary artery disease, Interventional cardiology and surgery, Heart, 2005, pp. 1047-1052, vol. 91—Iss. 8, BMJ Journals.

Six, A.J., et al., Chest pain in the emergency room: value of the HEART score, Netherlands Heart Journal, Jun. 2008, pp. 191-196vol. 16—No. 6.

Cervellin, G., et al., Diagnostic algorithms for acute coronary syndrome—is one better than another? Annals of Translational Medicine, May 2016, 6 pages, vol. 4—No. 10.

Coodacre, S., et al., The health care burden of acute chest pain, Heart, 2005, pp. 229-230, 91(2).

Goodacre, S., et al., Cost effectiveness of diagnostic strategies for patients with acute, undifferentiated chest pain, Emergency Medicine Journal, 2003, pp. 429-433, 20(5).

Penumeisa, S.C., et al., Outcomes of Patients Admitted for Observation of Chest Pain, Archives of Internal Medicine, May 7, 2012, pp. 873-877, vol. 172—No. 11.

Sharif, S., et al., Does This Patient With Chest Pain Have Acute Coronary Syndrome?, Annals of Emergency Medicine, Jul. 2017, pp. 44-45, vol. 70—No. 1.

Tang, E., et al., Global Registry of Acute Coronary Events (GRACE) hospital discharge risk score accurately predicts long-term mortality post acute coronary syndrome, American Heart Journal, Jan. 2007, pp. 29-35, vol. 153—No. Elsevier.

Than, M., et al., What is an acceptable risk of major adverse cardiac event in chest pain patients soon after discharge from the Emergency Department? A clinical survey, International Journal of Cardiology, 2012, pp. 752-754, vol. 166—No. 3, Elsevier.

Rajkomar, A., et al., Scalable and accurate deep learning with electronic health records, Digital Medicine, May 8, 2018, pp. 1-10, vol. 1—No. 18, nature partner journals.

Weiss et al. "Machine learning tor personalized medicine: predicting primary myocardial infarction from electronic health records," AI Magazine, 2012, vol. 33, No. 4, pp. 33-45.

Mochão, Hugo et al., "IPOscore: Art interactive web-based platform for postoperative surgical complications analysis and prediction in the oncology domain". Computer Methods and Programs in Biomedicine 219 (2022) 106754. 15 pages.

* cited by examiner

PATIENT TRACKERBOARD TOOL AND INTERFACE

BACKGROUND

The present technology relates generally to electronic records maintained by hospitals and other health care facilities for patients and used by those providing health care services to the patients, such as physicians, administrative staff, scribes, and other clinicians working in the hospitals, clinics and other health care facilities. Such electronic records may be stored and maintained by hospitals and health care facilities as part of health care computing systems, such as Electronic Medical Record (EMR) and Electronic Health Record (EHR) related technology (herein, the term "EMR" is intended to include both EMR and EHR).

For patients admitted to hospitals for treatment, such as patients admitted to hospital emergency departments, for example, health care providers often desire to keep a running list of patients prior to discharge. Prior to this invention, health care providers had to manually identify patients currently in the emergency department, and/or rely on a limited information read-only list of patient records, such as from a historical database, to track their patients.

Disadvantages of this process potentially include, among other things, time taken in generating patient lists, timeliness of providing the patient lists, limited information provided along with the patient lists, resource heavy access of a historical batch database to generate such a list, as well as potential error due to an inconsistent registration process, which is impossible to correct, update or overwrite in real-time or near real time, relative to data entry.

SUMMARY

Some embodiments of the present invention provide an automatically generated list of patients currently in the emergency department, combining real time data and historical or analytics data, with writeback functionality. In some embodiments, real time data is combined with supplementary or other data. Real time data includes patient encounter details, patient codes, provider, patient, patient insurance, and the like, entered during the registration process. Supplementary or other data includes disease management information, high risk modeling, six-month count, provider daily schedule and the like. In some embodiments, data is written back or updated, from user input via an interface, including provider assignment, or disease management information, or the like.

According to one embodiment, a computer-implemented system is provided for use with Electronic Medical Records (EMRs), the system comprising a parser engine configured to receive, in real time or near real time relative to entry of EMR data into an EMR system, Health Level 7 (HL7) messages including the EMR data, and using parsing logic, parse, in real time or near real time relative to entry of the EMR data, the HL7 messages to identify and extract specified EMR data therefrom, a database configured to, in real time or near real time relative to entry of the EMR data, receive and store parsed data comprising the extracted specified EMR data, a presentation engine configured to display a trackerboard, wherein the trackerboard includes a graphical user interface that presents collected patient data, and wherein the collected patient data comprises a list of patients currently admitted to an emergency department of a medical facility or hospital, wherein the list of patients is determined using patient data obtained from the parsed data, and analytic EMR data relating to each patient in the list of patients, wherein the analytic EMR data is obtained from analysis of, at least, obtained historical EMR data relating to each of the patients, wherein the collected patient data is periodically refreshed based on the parsed data and edits received via user interaction with the trackerboard.

According to one embodiment, a computer-implemented method is provided for use with Electronic Medical Records (EMRs), the method comprising receiving, by a parser engine, in real time or near real time relative to entry of EMR data into an EMR system, Health Level 7 (HL7) messages including the EMR data, and using parsing logic, parsing, by the parser engine, in real time or near real time relative to entry of the EMR data, the HL7 messages to identify and extract specified EMR data therefrom, receiving and storing by a database parsed data comprising the extracted specified EMR data, in real time or near real time relative to entry of the EMR data, displaying a trackerboard by a presentation engine, wherein the trackerboard includes a graphical user interface that presents collected patient data, and wherein the collected patient data comprises a list of patients currently admitted to an emergency department of a medical facility or hospital, wherein the list of patients is determined using patient data obtained from the parsed data, and analytic EMR data relating to each patient in the list of patients, wherein the analytic EMR data is obtained from analysis of, at least, obtained historical EMR data relating to each of the patients, wherein the collected patient data is periodically refreshed based on the parsed data and edits received via user interaction with the trackerboard.

According to one embodiment, a non-transitory computer readable medium or media is provided containing instructions for executing a method for use with Electronic Medical Records (EMRs), the method comprising receiving, by a parser engine, in real time or near real time relative to entry of EMR data into an EMR system, Health Level 7 (HL7) messages including the EMR data, and using parsing logic, parsing, by the parser engine, in real time or near real time relative to entry of the EMR data, the HL7 messages to identify and extract specified EMR data therefrom, receiving and storing by a database parsed data comprising the extracted specified EMR data, in real time or near real time relative to entry of the EMR data, displaying a trackerboard by a presentation engine, wherein the trackerboard includes a graphical user interface that presents collected patient data, and wherein the collected patient data comprises a list of patients currently admitted to an emergency department of a medical facility or hospital, wherein the list of patients is determined using patient data obtained from the parsed data, and analytic EMR data relating to each patient in the list of patients, wherein the analytic EMR data is obtained from analysis of, at least, obtained historical EMR data relating to each of the patients, wherein the collected patient data is periodically refreshed based on the parsed data and edits received via user interaction with the trackerboard.

While the invention is described with reference to the above drawings, the drawings are intended to be illustrative, and the invention contemplates other embodiments within the spirit of the invention.

DETAILED DESCRIPTION OF EMBODIMENTS OF THE PRESENT INVENTION

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

Any process described in this application may be performed in any order and may omit any of the steps in the process. Processes may also be combined with other processes or steps of other processes.

Figure 1:
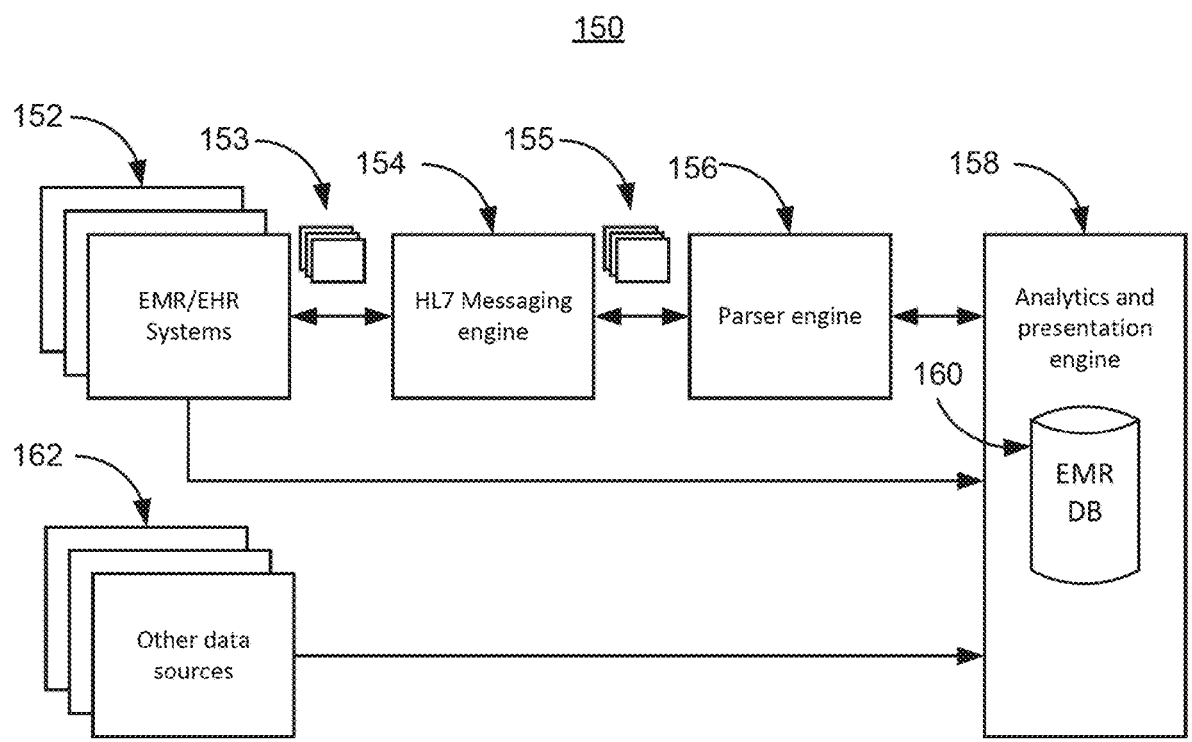
FIG. 1 illustrates a block diagram of an architecture of a system according to some embodiments of the invention.

FIG. 1 illustrates a block diagram of an architecture 150 of a system according to some embodiments of the invention. Depicted are multiple EMR/EHR systems 152, other data sources 162, an HL7 messaging engine 154, a parser engine 156 and an analytics and presentation engine 158. In various embodiments, elements such as the EMR/EHR systems 152, the other data sources 162 and the HL7 messaging engine 154, or portions thereof, may or may not themselves be part of the inventive system. For example, in some embodiments, the parser engine 156 only, or operation thereof, or elements of the parser engine 156, or elements of operation thereof, may constitute an entire inventive system, method, apparatus, architecture, data structure, computer readable media, etc.

It is to be understood that intermediary entities may be present in addition to those depicted, or multiple separate sub-entities of particular entities, and data may be received and sent from such non-depicted intermediaries or sub-entities to, from or within depicted entities, such as from the EMR/EHR systems 152 or the other data sources 162. It is further to be understood that, while a single HL7 messaging engine 154, parser engine 156 and analytics and presentation engine 158 are depicted, each engine can be implemented by or using one or more networks, computers, servers, clients, applications, operating systems, software, hardware, etc., as well as various communications therebetween.

The EMR/EHR systems 152 may be located at or associated with various sites, such as hospitals, medical facilities, doctor's offices, etc. EMR data may be entered, logged, recorded or input at such sites. For example, upon admission of a patient into a hospital, EMR data relating to the patient, e.g. patient's name, patient's demographics, billing information, insurance information, health-related complaint, lab tests ordered for diagnosis, collected vitals or other data, and many other types of data, may be entered, recorded or logged, or collected and entered, recorded or logged, into the hospital's computerized EMR system. In addition, other types of EMR data may be entered.

EMR data entered or logged into the EMR/EHR systems 152 may immediately, such as in real time or near real time, be sent as a stream of data items or HL7 messages 153 to the HL7 messaging engine 154, directly, indirectly or via intermediary entities. Depending on specific circumstances, real time or near real time can be, for example, within seconds or a fraction of a second. In various embodiments, the EMR data sent from the EMR/EHR systems 152 may be in various forms and formats, such as not yet formatted into HL7 messages, partially formatted into HL7 messages, or fully formatted into HL7 messages.

In various embodiments, the HL7 messaging engine 154 may serve a variety of functions, such as relating to formatting, structuring or serializing, or re-formatting, re-structuring or re-serializing or sending, for example, EMR data not in the form of HL7 messages, partial or incompletely formatted or structured HL7 messages, or complete or fully structured HL7 messages. However, in some embodiments, an HL7 engine may be omitted, and HL7 messages may be sent directly or indirectly to the parser engine 156 without first being sent to an HL7 messaging engine 154. Furthermore, in some embodiments, the parser engine 156 alone, or certain elements thereof, may perform all inventive steps or may constitute the entire inventive architecture, method, system, computer readable media, etc. In other embodiments, the parser engine 156 or elements thereof, or other engines or elements other than the parser engine 156, may constitute the entire inventive architecture, method, system, computer readable media, etc.

In some embodiments, the HL7 messaging engine 154 may be implemented, in whole or in part, using various tools and designs, such as, for example, a Mirth or Mirth Connect or Nextgen Connect cross-platform HL7 interface engine.

In some embodiments, the HL7 messaging engine 154 plays a role in, for example standardizing, unifying, or otherwise preparing for efficient and fast ingestion by the parser engine 156 of all or part of disparate or variously structured or formatted EMR data or HL7 messages originating from the various EMR/EHR systems 152. This can include, for example, accounting for, labelling or otherwise preparing for ingestion by the parser engine 156 HL7 messages with custom or z-segments specified by particular EMR systems or sites 152. Although embodiments of the invention are described herein generally with reference to HL7 messages, in some embodiments, EMR data or messages other than HL7 messages, or non-medical electronic records, are contemplated and utilized.

As depicted, HL7 messages 155 are sent or streamed from the HL7 messaging engine 154 to the parser engine 156. The parser engine 156 may immediately parse the HL7 messages to identify, locate (such as, within an HL7 message) and extract (which can broadly include copying, duplicating, sending, making use of, etc.) particular HL7 message data, such as using parser logic that may, for example, be embodied in software. The parser engine 156 may direct storage of the extracted HL7 message data in an EMR database 160 of the analytics and presentation engine 158, such as by using relational database interface logic that may, for example, be embodied in software. However, in some embodiments, the directing of the extracted data may be accomplished in whole or in part outside of the parser engine 156, such as in whole or in part by the analytics and presentation engine 158. In some embodiments, the parser engine 156 may direct storage of extracted EMR data as appropriate, optimal or efficient, in tables of the EMR database 160, with logic taking into account the design and structure of the EMR database 160.

The EMR database 160 may be any of various types of data stores and databases, and may or may not be a relational database. In some embodiments, various relational database management systems (RDBMS), tools, applications, programming and programming languages may be used in connection with the EMR database 160 and the directing of extracted data to and from the database 160, such as, for one of many possible examples, SQL (Structured Query Language). The EMR database 160, as well as database management and tools, may be designed and structured, in whole or in part, to accommodate, speed, make more efficient, or optimize its use according to embodiments of the invention.

For various clinical, medical, or health care related needs, requests or uses, the analytics and presentation engine 158 may query the EMR database 160 for needed EMR data. In some embodiments, the EMR database 160 may contain both real-time or near real time data represented as data that has passed through the parser engine 156, and other data, represented as data that has not passed through the parser engine 156. Furthermore, the analytics and presentation engine 158 may use, in determining analytic results data, for example, data from EMR/EHR systems 152 and data from other data sources 162. The utilized data may include data originating as HL7 message data and other data.

The analytics and presentation engine 158 may then analyze or direct analysis of acquired or selected EMR data to determine or generate needed analytical results data, which may be dependent on the use case scenario. The analytical results data may be presented, including made available for presentation, such as display, to, for example, doctors or other medical professionals or medical staff. In determining the analytical result data, the analytics and presentation engine may use logic embodied in software, and may utilize both current, real time or near real time EMR data as well as historical, chronologically tracked EMR data from the EMR database 160. Presentation or display of analytical results data case broadly include presentations or displays that directly or indirectly communicate portions, elements or aspects of the analytical results data, directly or indirectly, or data derived therefrom.

The EMR database 160 may be designed or structured, in whole or in part, to best accommodate its anticipated uses for clinical, medical, or health care related needs, requests or uses according to embodiments of the invention. For example, the tables, views and other structuring elements of the EMR database 160 may be designed and configured to best, quickly, efficiently or optimally enable determination of analytical results data, such as for particular clinical, medical, or health care related needs, requests or uses. For example, in some embodiments, tables that may receive extracted data may include one or more tables with each of patient data, patient encounter data, patient insurance data, insurance provider data, patient codes, clinical event data, clinical lab result data, order data, and others.

Furthermore, in some embodiments, various elements of the overall architecture 150 are designed to function optimally together. For example, aspects of each of various elements, such as the EMR/EHR systems 152, the other data sources 162, the HL7 messaging engine 154, the parser engine 156 and the analytics and presentation engine 158, and logic relating to each, may be designed to operate, communicate or interface quickly, efficiently or optimally with various of the other elements, as well as particular actual, possible, or anticipated clinical, medical, or health care related needs, requests or uses. Aspects of clinical, medical, or health care related needs, requests or uses can include, for instance, the analytic substance of the needed analytic results data (e.g., analytic results data relating to the probability of chest pain being associated with a heart-related event), medical end users and sites, end user or site electronic systems, and many other things. Furthermore, in some embodiments, the HL7 messaging engine 154 and the parser engine 156 design may take into account aspects of each other, as well as aspects of the EMR/EHR systems 152 (such as the formatting and structuring specifics of EMR data or HL7 messages coming from each of them), the other data sources, intermediaries, the design and structure of the analytics and presentation engine 158 and the EMR database 160 (including tables and views structures, for instance), particular actual, possible or anticipated clinical, medical, or health care related needs, requests or uses, and types of analytic results data.

In some embodiments, the design of the overall architecture 150 allows determination and presentation of needed analytic results data for particular clinical, medical, or health care related needs, requests or uses in real time or near real time relative to a time of entry of relevant current EMR data at EMR/EHR systems 152, or relative to a time of sending of the EMR data to the HL7 messaging system 154 or parser engine 156. In some embodiments, the relevant current EMR data can include the most current EMR data needed in determination of the needed analytic results data for a particular use case scenario, which can be used, in some cases, in addition to relevant historical EMR data. In some embodiments, relevant EMR data be determined in whole or in part by the analytics and presentation engine 158. It is to be noted that analytic results data can, in various embodiments, include any desired results data that results from analysis of EMR data.

In general, in various embodiments, various elements of operation of the inventive architecture 150 may operate or produce results faster than previously existing architectures. Such results can include determination and presentation of analytic results data, or other particular results or outcomes, such as parsing of an HL7 message by a parser engine to identify and extract needed or desired EMR data, for example.

In some embodiments, various forms of machine learning and machine learning models and feature sets may be used in various aspects of the architecture 150 and its operation. For example, machine learning may be utilized in building, updating or optimizing, such as periodically or continuously, the HL7 messaging engine 154 or its logic, the parser engine 156 or its logic, or the analytics and presentation engine 158 or its logic, which could include the EMR database 160 format and structure, including overall and individual table and view structures or designs, definitions and configurations, etc. In some embodiments, machine learning techniques are used in connection with current and historical EMR data stored, or other data, in the EMR database 160, potentially among other data.

In some embodiments, data received by, stored in, and potentially merged or integrated in the database 160, such as in tables and views, can include data from various sources. These sources are depicted generally as the EMR/EHR systems 152, as well as the other data sources 162 that can include any sources other than the EMR/EHR systems 152. Furthermore, it is to be understood that data from the EMR/EHR systems 152 and other data sources 162 may be received directly by the database 160, or may first pass through, and potentially be modified or transformed by, one or more intermediaries, such as various intermediary systems or entities. For example, in some cases, data from the EMR/EHR systems 152 may first pass through an intermediary billing-related entity.

Data received by the database 160 from the EMR/EHR systems 152 can include data obtained from HL7 message data or from non-HL7 data. In some embodiments, non-HL7 data does not pass through the HL7 messaging engine 154 or the parser engine 156, prior to being received by the database 160. In some embodiments, non-HL7 message data may be sent from the EMR/EHR systems 152 or the other data sources to EMR database 160 directly or after passing through and potentially being modified or transformed by intermediaries. For example, non-HL7 message data sent by the EMR/EHR systems 152, and not passing through the HL7 messaging engine 154 or the parser engine 156, may include non-real-time or non-near real-time, historical, batch, or periodically or intermittently sent data, where the period or frequency of sending or receipt, whether regular or irregular, can vary greatly. For example, the frequency might be a small fraction of second, one or more seconds, one or more minutes, one or more hours, one or more days, or even longer.

Other data, from the other data sources 162, can include non-public or public source data. The other data can include, for example, billing or insurance-related data. In some embodiments, the other data can include public data that may be used in connection with billing, insurance, health care or medical care providers, or other entities, parties, or aspects of medical or health care, or medical or health care data. For example, in some embodiments, public data may be used in connection with various stored data, such as for data enrichment or supplementation, or in connection with, or to confirm or verify, for example, registrations, licensing or name validation, in connection with providers, insurance companies, billing or billing companies, codes and coding, other parties or entities. For example, in some embodiments, data, such as codes or standards, may be obtained from public databases such as LOINC (Logical Observation Identifiers Names and Codes), or from sources associated with other standards or coding entities, such as National Provider Identifier Standard (NPI) data, for instance.

Figure 2:
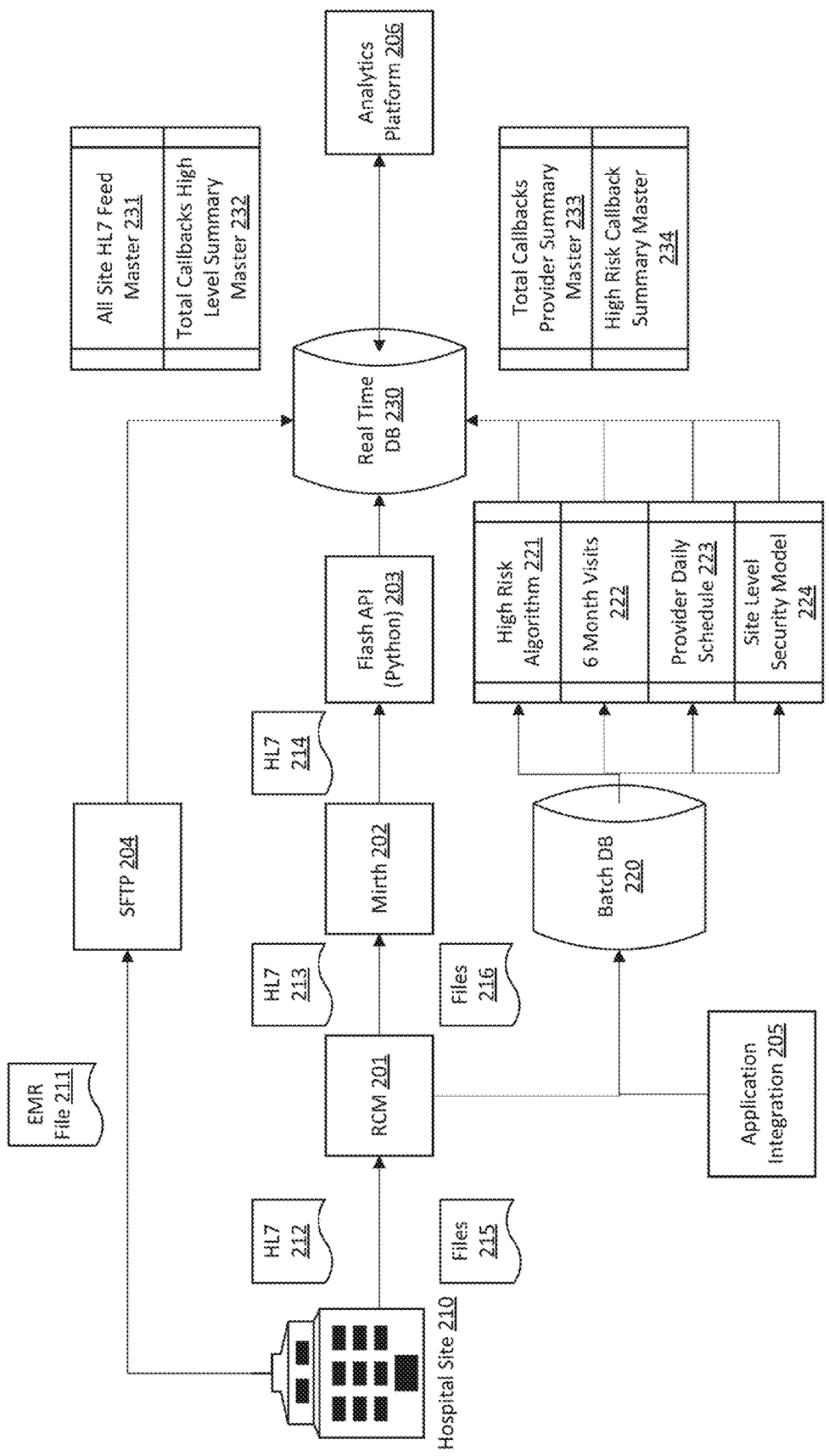
FIG. 2 illustrates a block diagram of the data flow and architecture of a system according to some embodiments of the invention.

FIG. 2 illustrates a block diagram of the data flow and architecture of a system according to some embodiments of the invention. Scribes, physicians or nurse practitioners log healthcare encounter events into EMR systems at Hospital Site 210, including for example, patient demographics and lab tests. Hospital Site 210 transmits patient detail files, including HL7 212 and Files 214 to a data engineering team at Revenue Cycle Management (RCM) 201 for processing. The HL7 212 file may include raw HL7 stream data generated by the EMR system. The files may document which patients have been diagnosed with conditions for disease management. HL7 212 file may include real time data that is transferred via HL7 messages from the Hospital Site 210.

The files are then sent as HL7 213 to Mirth 202 for further processing. Mirth 202 may include a server for processing HL7 messages. Mirth 202 server sends HL7 214 as re-serialized in HTTP Body payload. Once the file HL7 214 leaves the Mirth server, it proceeds to Flash API (Python) 203, which may be an API and a python application. In some embodiments, Mirth 202 may include an open source tool that implements MLLP protocol which formats HL7 messages and gives it a structure. In some embodiments, Mirth 202 recognizes when a HL7 message starts and stops. In some embodiments, Mirth 202 ingests data from upstream hospitals and serves as input to the Flash API (Python) 203. In some embodiments, Flash API (Python) 203 uniquely identifies different segments present in a single HL7 message and parses data based on locations predefined by HL7 specification along with custom locations supported by the site.

The Files 215 are sent to Batch DB 220. In some embodiments, Batch DB 220 may include Provider Daily Schedule 223, and 6 Month Visits 222 which may include emergency department visits for the past six months, Site Level Security Model 224, and High Risk Algorithm 221. In some embodiments, the aforementioned information may be available in HL7 data and the system first checks for availability in HL7 before querying the Batch DB 220. For example, the information from the 6 Month Visits 222 field may already be in HL7 data. Provider Daily Schedule 223 is scheduling information that documents each provider's shifts, when they work, how long they work, respective facilities, and the like. This information may be summarized to calculate the number of shifts each provider at each site has per month. In some embodiments, schedule information is summarized to calculate the number of shifts each provider at each site has per month. In some embodiments, Site Level Security Model 224 includes row level security which restricts data access based on a user's credentialed sites or locations and roles at those respective sites or locations. Access is maintained and audited by a centralized security administration team which is responsible for provisioning, reviewing, and terminating access to applications.

In some embodiments, Batch DB 220 may include a billing database, historical data, data received from revenue cycle management entities, data loaded in batches, for example, once a month, including data for multiple, for example hundreds of sites. In some embodiments, Batch DB 220 is populated periodically at a predetermined time interval such as daily, weekly, monthly or another time interval.

EMR File 211 is data from the Hospital Site 210 that is sent via the SFTP 204 protocol to the Real Time DB 230 database. In some embodiments, EMR File 211 includes a direct load of a flat file provided by the hospital from their EMR system to enrich existing data for use in disease management. For example, the list of diagnosis codes to flag patients with specific diseases are hospital specific and allows for maximum flexibility.

The Real Time DB 230 database includes EMR data (e.g., EMR File 111), historical data (e.g., from Batch DB 220) and HL7 real-time data (e.g., HL7 212, HL7 213, HL7 214) and provides various views or datasets such as All Site HL7 Feed Master 231 (the main source for trackerboard), Total Callbacks High Level Summary Master 232, Total Callbacks Provider Summary Master 233, and High Risk Callback Summary Master 234. In some embodiments, All Site HL7 Feed Master 231 joins real time HL7 data and batch DB, and historical data to provide a real time patient list of patients currently in the emergency department. The Analytics Platform 206 may use the data in Real Time DB 230 for presentation. The Analytics Platform 206 and the Real Time DB 230 may have a bi-directional connection. In some embodiments, the Analytics Platform 206 may write back data or override data to Real Time DB 230, for example, when a user enters provider attribution via an interface. The Analytics Platform 206 may provide a customizable patient list for patients currently in the emergency department, including details about their visit history, high risk determination, diagnosis.

Application Integration 205 refers to internal system application integration used in some embodiments of the invention, integrating internal data sets containing user information (name, NPI, exchange directory name, hospital site affiliation), provider scheduling, and other enterprise data with the internal system applications. In some embodiments of the invention, these internal data sources may range from enterprise applications such as SalesForce to health care facility patient and provider scheduling platforms. Internal data for application integration may be received in a batch process and leveraged for developing user security, provider analytics for shifts worked and calculating their benchmarks based on threshold X number of shifts worked. In one embodiment of the invention, a default goal for the application is 2 callbacks per provider per shift of work. In some embodiments of the invention, the default goal can be customized by medical administrators or directors using a configuration panel for the tool suite.

Figure 3:
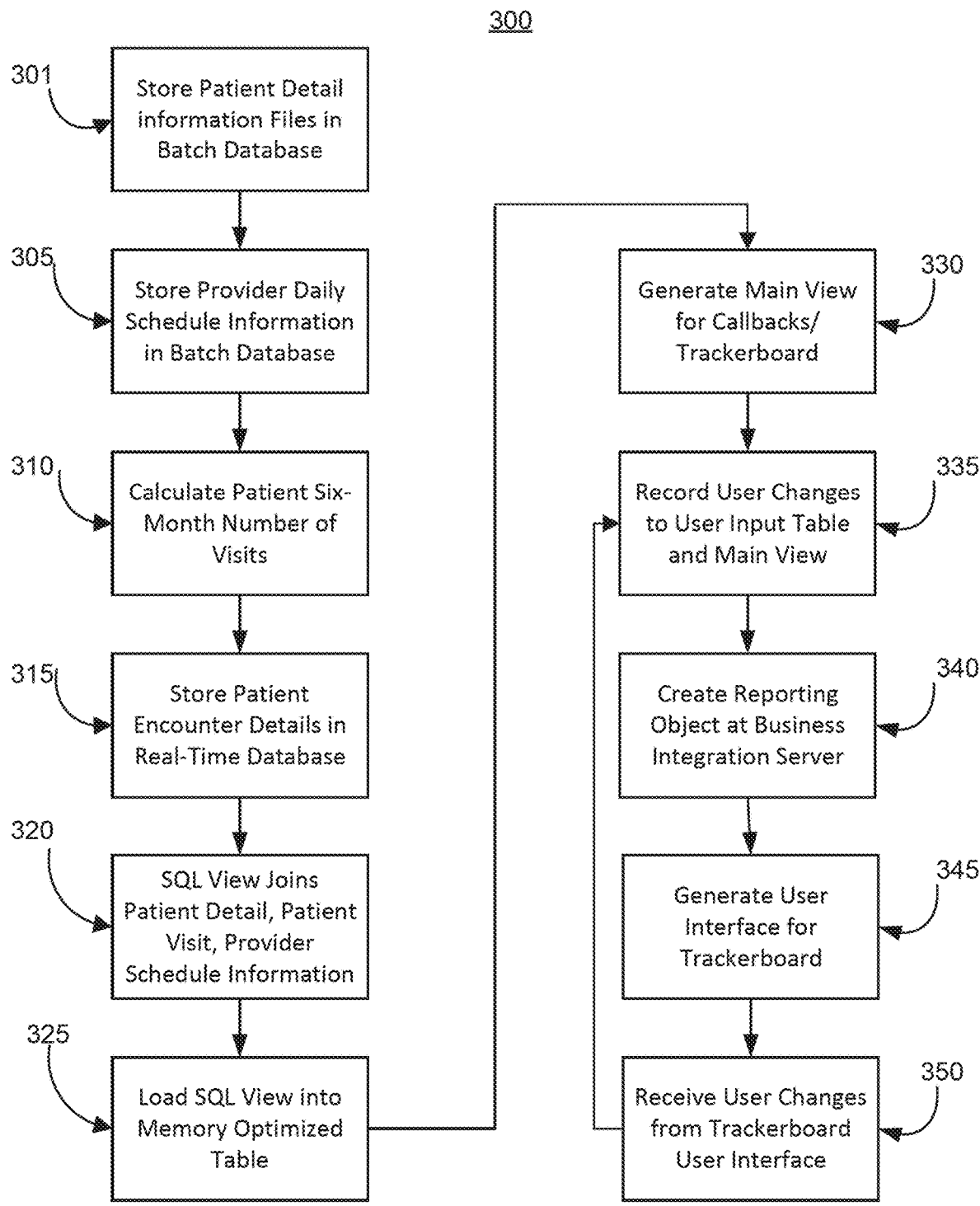
FIG. 3 illustrates a flow diagram of a method according to some embodiments of the invention.
Figure 5:
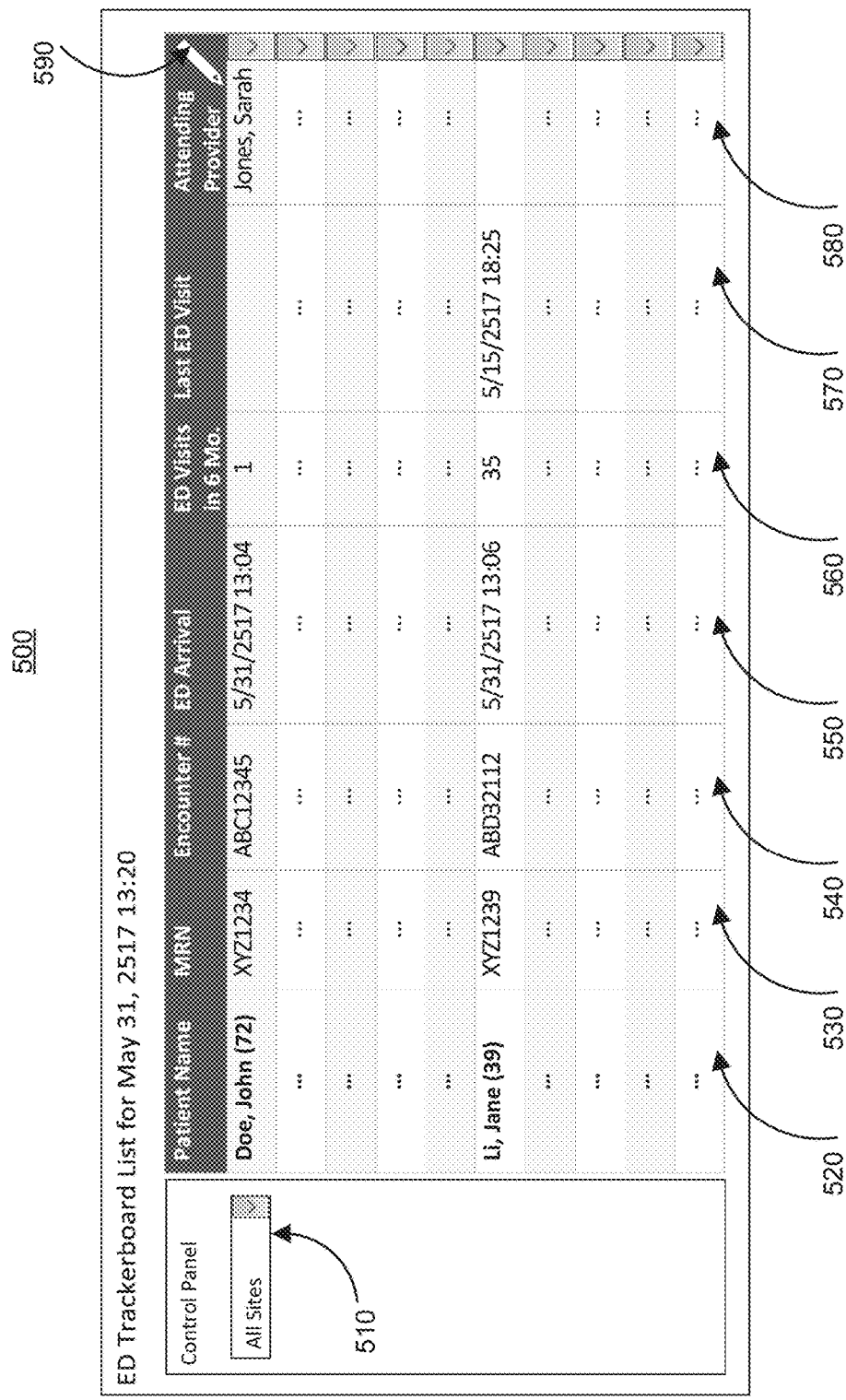
FIG. 5 illustrates a screenshot of an exemplary user interface display according to some embodiments of the invention.

FIG. 3 illustrates a flow diagram of a method according to some embodiments of the invention and describes the data flows that were shown in FIG. 5 as network connections. In step 301, daily batch data feeds for patient records are retrieved from EMR database 110 and stored in the batch database 120. In step 305, provider daily schedule information is stored in the batch database 120. In step 310, patient detail information stored in the batch database 120 is used to calculate patient six-month number of visits. In step 315, streaming HL7 messages relevant to patient encounter details are stored in real-time database 130. In steps 220 and 225, the daily batch data feeds from batch database 120 including patient detail information and provider daily schedule information, the patient encounter details and provider daily schedule information in real-time database 130, and patient six-month visit information are passed to SQL view and memory optimized table 140. In step 330, the main SQL views for the trackerboard tools are generated. In step 335, user changes to the main view for the trackerboard tools may be recorded, as well as user changes to the user input table. In step 340, a reporting object is created at BI server 155. In step 345, the user interface for the callbacks and/or trackerboard tools is generated at user interface server program 155 and may be displayed on a user interface client of clinician user device 160. From time to time, user interface client of clinician user device 160 may also receive updates and changes to the patient and provider data shown in the client user interface, which is then updated in step 335.

Figure 4:
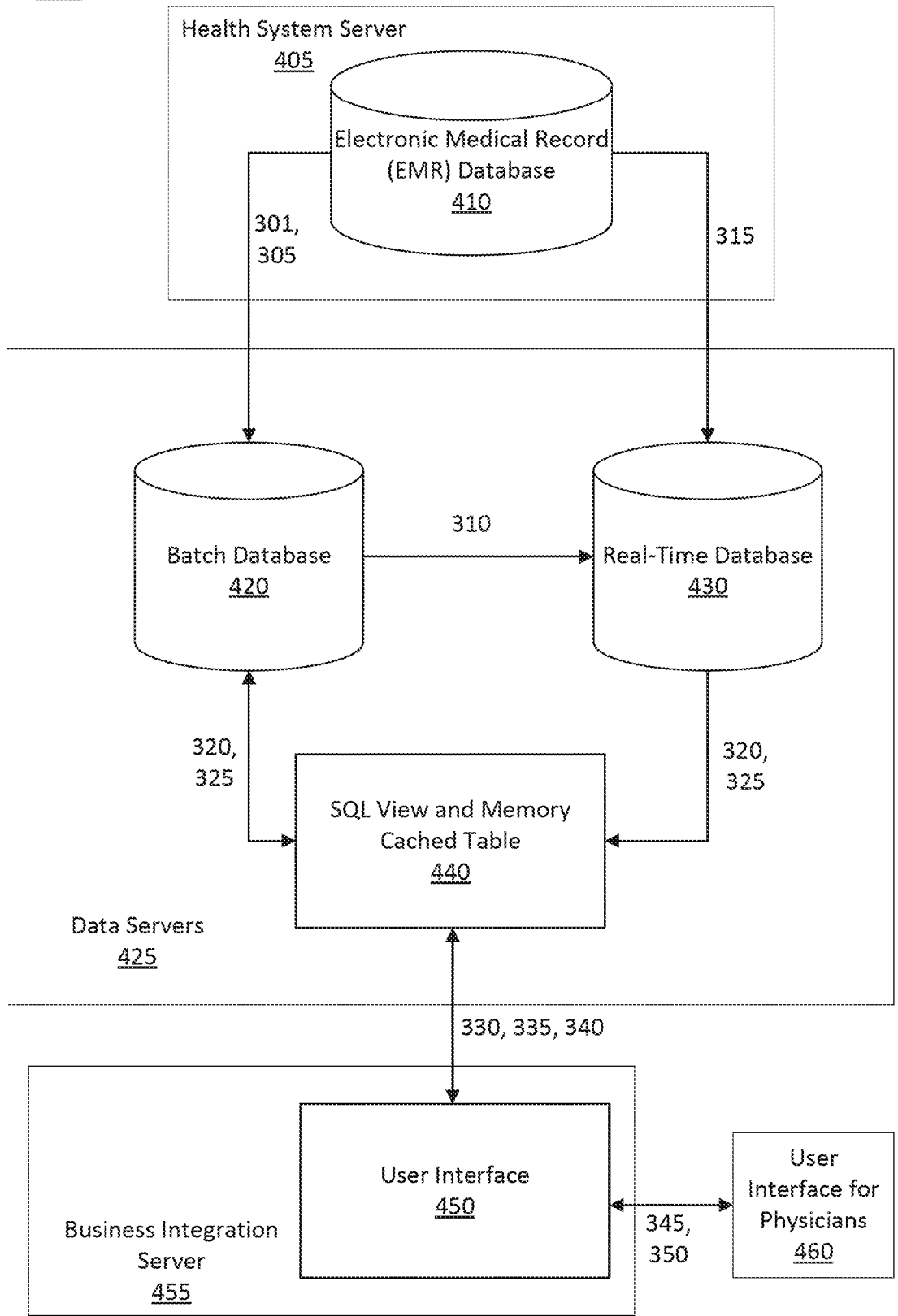
FIG. 4 illustrates a block diagram of the data flow and architecture of a system according to some embodiments of the invention.

FIG. 4 illustrates a block diagram of the data flow and architecture of a system 400 according to some embodiments of the invention. Depicted are one or more health system servers 405, one or more data servers 425, including a batch database 420, a real-time database 430, an SQL and Memory Cached Table 440. Data servers 425 are operably connected to Business Integration (BI) server 455 having a user interface server program 450, which is in turn operably connected to one or more exemplary user devices, each including a user interface for physicians 460. In various embodiments, elements such as the health system servers 405 and user devices 460, or portions thereof, may or may not themselves be part of the inventive system. For example, in some embodiments, the SQL and memory cached table 440 only, or operation thereof, or elements of the SQL and memory cached table 440, or elements of operation thereof, may constitute an entire inventive system, method, apparatus, architecture, data structure, computer readable media, etc.

It is to be understood that intermediary entities may be present in addition to those depicted, or multiple separate sub-entities of particular entities, and data may be received and sent from such non-depicted intermediaries or sub-entities to, from or within depicted entities. It is further to be understood that, while a single health system server 405, data server 425, SQL view and memory cached table 440, business integration (BI) server 455, and user device 460 are depicted, each engine can be implemented by or using one or more networks, computers, servers, clients, applications, operating systems, software, hardware, etc., as well as various communications therebetween.

Health system servers 405 receiving and storing EMR data may be located at or associated with various sites, such as hospitals, medical facilities, doctor's offices, etc. EMR data may be entered, logged, recorded or input at such sites. For example, upon admission of a patient into a hospital, EMR data relating to the patient, e.g. patient's name, patient's demographics, billing information, insurance information, health-related complaint, lab tests ordered for diagnosis, collected vitals or other data, prescriptions, diagnoses, surgery history, and many other types of data, may be entered, recorded or logged, or collected and entered, recorded or logged, into the hospital's computerized EMR system. In addition, other types of EMR data may be entered.

EMR data entered or logged into the health system servers 405 may immediately, such as in real time or near real time, be sent as a stream of data items directly, indirectly or via intermediary entities. Depending on specific circumstances, real time or near real time can be, for example, within seconds or a fraction of a second. In various embodiments, the EMR data sent from the health system servers 405 may be in various forms and formats, such as not yet formatted into HL7 messages, partially formatted into HL7 messages, or fully formatted into HL7 messages. EMR and other data present in health system servers 405 may be transmitted to data servers 425 and/or SQL view and memory cached table 440 where one or more machine learning models may operate on the EMR data to derive risk estimates for, e.g. acute coronary syndrome (ACS) or other medical conditions, diagnoses, or diseases for one or more patients. BI server 455 compiles incoming query requests from users (e.g. emergency department physicians and other clinicians) via a user interface client running on user device 460 and translates the data to SQL or other readable query format and sends the request to back-end databases at data servers 425 and modeling servers 430. BI server 455 will also receive the query results and prepare the data results for display on the user interface running on user device 460.

Health system server 405 includes one or more EMR databases 410. Health system server 405 is connected to one or more data servers 425. In various embodiments of the invention as discussed above, one or more data and model servers 425 comprise a batch database 420 and real-time database 430. Batch database 420 may be operably connected to health system server 405 and may receive batch data at pre-specified time intervals from EMR database 410 via network connection 301 and 305. In various embodiments of the invention, real-time database 430 may also be operably connected to health system 405 and may receive data in real-time or near real-time upon user request via network connection 315. Batch database 420 may also be operably connected to SQL view and memory cached table 440 via network data connections 320 and 325, and to real-time database 430 via network data connections 320 and 325. Real-time database 430 is also connected batch database 420 via network data connection 310. SQL view and memory cached table 440 is also operably connected to business integration server 455 running user interface server program 450 via network data connection 330, 335 and 340. BI server 455, via user interface server 450, is also operably connected to the user interface running on user device 460 through network connections 345 and 350.

FIG. 5 illustrates a screenshot of an exemplary user interface display according to some embodiments of the invention. The user interface dashboard 500 is generally designed to be available to clinicians in the emergency department, and in some embodiments of the present invention, comprise a table having rows and columns, where each row corresponds to one patient in the emergency department. The user interface dashboard 500 is updated in real time or near real time. In some embodiments, a record is created for all emergency department patients regardless of disposition. That is, user interface dashboard 500 shows all emergency department encounters as they arrive in the emergency department and disposition has not been made on these patients, as it will show patients who will eventually be discharged or possibly admitted. In some embodiments, each row corresponds to one patient record including patients that were seen up to 12 hours from emergency department arrival time 550. In some embodiments, after 12 hours, the patient will be removed from the list.

The user interface dashboard 500 may display filtered results based on selected sites 510, which may be a field configured as a drop down allowing to filter the patients by their location, including for the location of the emergency department. In some embodiments, a site must be selected before entering data user interface dashboard 500 and if the site is empty, then the information may not be properly saved. The patient name 520 column includes a customizable field displaying at least a patient's first and last name. In some embodiments, the patient name 520 field may also include the patients age, in parenthesis, after the name. The MRN 530 column includes a medical record number for patients and encounters. The encounter number 540 column includes an identifier for a patient encounter. In some embodiments, the encounter number 540 is numeric or alphanumeric and may be randomly or serially generated or queried from a database. The emergency department arrival time 550 column includes the patient's arrival date and/or time into the emergency department. The emergency department visits in 6 months 560 column includes a count of emergency department visits for the patient in the last 6 months. The last emergency department visit 570 column includes the last date and/or time the patient visited the emergency department. In some embodiments, the date and time related fields include automated time stamps. The attending provider 580 column includes the name of a provider recently or currently assigned to the patient. The provider edit icon 590 allows you to update the provider information for all patients.

In some embodiments, there may be additional fields and settings such as override and hybrid fields or settings (not illustrated). When activating the override setting, this setting will completely ignore the HL7 feed and will require overrides from the user interface dashboard 500, including for example attributing patients to a provider. When activating the hybrid setting, this setting will leverage the HL7 messages as is but also accept overrides from the user interface dashboard 500. Attribution will default to HL7 unless an override is completed. In some embodiments, there may be additional fields related to health risks (not illustrated). For example, for patients presenting in the emergency department with unspecified chest pain may have a cardiac predictive risk estimate and predicted outcome displayed in an additional field or column, for example, as a check box. In some embodiments, the user interface dashboard 500 refreshes periodically, for example, every five minutes. In some embodiments, there may be a submit button which may appear upon making entries or changes into and be used for updating the user interface dashboard 500. In some embodiments, unsubmitted information may be lost in the case of a refresh. Other patent applications describe exemplary embodiments of this user interface display in detail, including, but not limited to, co-pending U.S. patent application Ser. No. 16/378,460, filed on Apr. 8, 2019, which is herein incorporated by reference in its entirety.

The user interface dashboard 500 and the trackerboard tool allows for patient information processing acceleration techniques to improve system performance, reduce performance variability, increase capacity and throughput, while also preferably reducing the physical and power requirement footprint and lowering the cost of implementation. The user interface dashboard 500 and the trackerboard tool overcomes the constraints of traditional computing concepts associated with EMR-owned patient lists related to limited write-back functionality, moving data from one server to another, or moving data between physical components within a single server, or between different applications or processes within a single server. Such traditional computing concepts can introduce capacity and performance constraints, which may be partially or wholly overcome by utilizing the EMR-agnostic trackerboard tool which can take HL7 data from any EMR system and display the records for scribes and providers, as described herein in the context of the various embodiments.

By way of non-limiting example, the systems and methods of the various embodiments of the invention described herein reduce the processing duplication that occurs in traditional electronic patient information management infrastructure and reflect a departure from the traditional paradigm of standardized EMR-based processing. The trackerboard tool and user interface dashboard 500 reduces the number of processing steps, including the need for traditional EMR processing mechanisms. The trackerboard tool and user interface dashboard 500 also reduces the duplicative nature of entering and querying patient information records and a variety of other processing steps.

Figure 6:
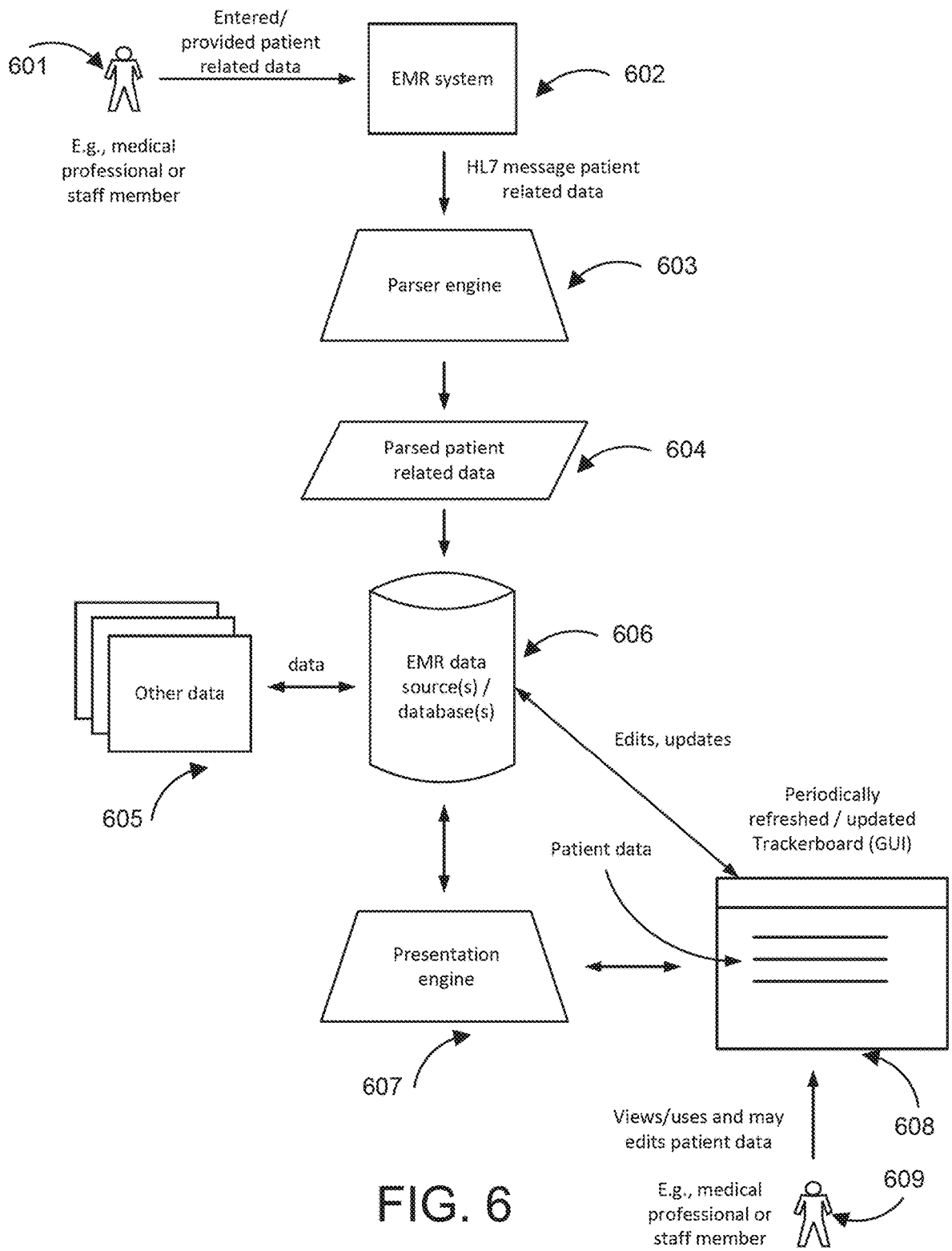
FIG. 6 illustrates a block diagram according to some embodiments of the invention.

FIG. 6 illustrates a block diagram according to some embodiments of the invention, including a parser engine 603 and a presentation engine 607. As depicted, a person 601, such as a medical professional, staff member, or a scribe, enters or otherwise provides patient related data into an EMR system 602. HL7 message data, including patient related data, is sent to a parser engine 603 (as further described in co-pending U.S. patent application Ser. No. 16/297,456, filed on Mar. 8, 2019, which is herein incorporated by reference in its entirety). The parser engine parses the HL7 message data 604 and sends the parsed patient-related data to an EMR data source(s) or database(s) 606. In addition to the parsed data, other data 605 including patient-related data from other data sources, such as may include historical patient related data, insurance or billing related data, etc., is sent to and stored in the EMR data source(s) or database(s) 606.

A presentation engine 607 collects data from the EMR data source(s) or database(s) 606, including parsed and other patient-related data, and uses the collected data to generate periodically updated trackerboard data and a periodically updated GUI-based trackerboard 608 made available or presented to a user 609, such as a medical professional, staff member or scribe. In some embodiments, the user 609 may update some of the information displayed on the trackerboard 608, and the edits are sent to, and used to update, the EMR data source(s) or database(s) accordingly.

Figure 7:
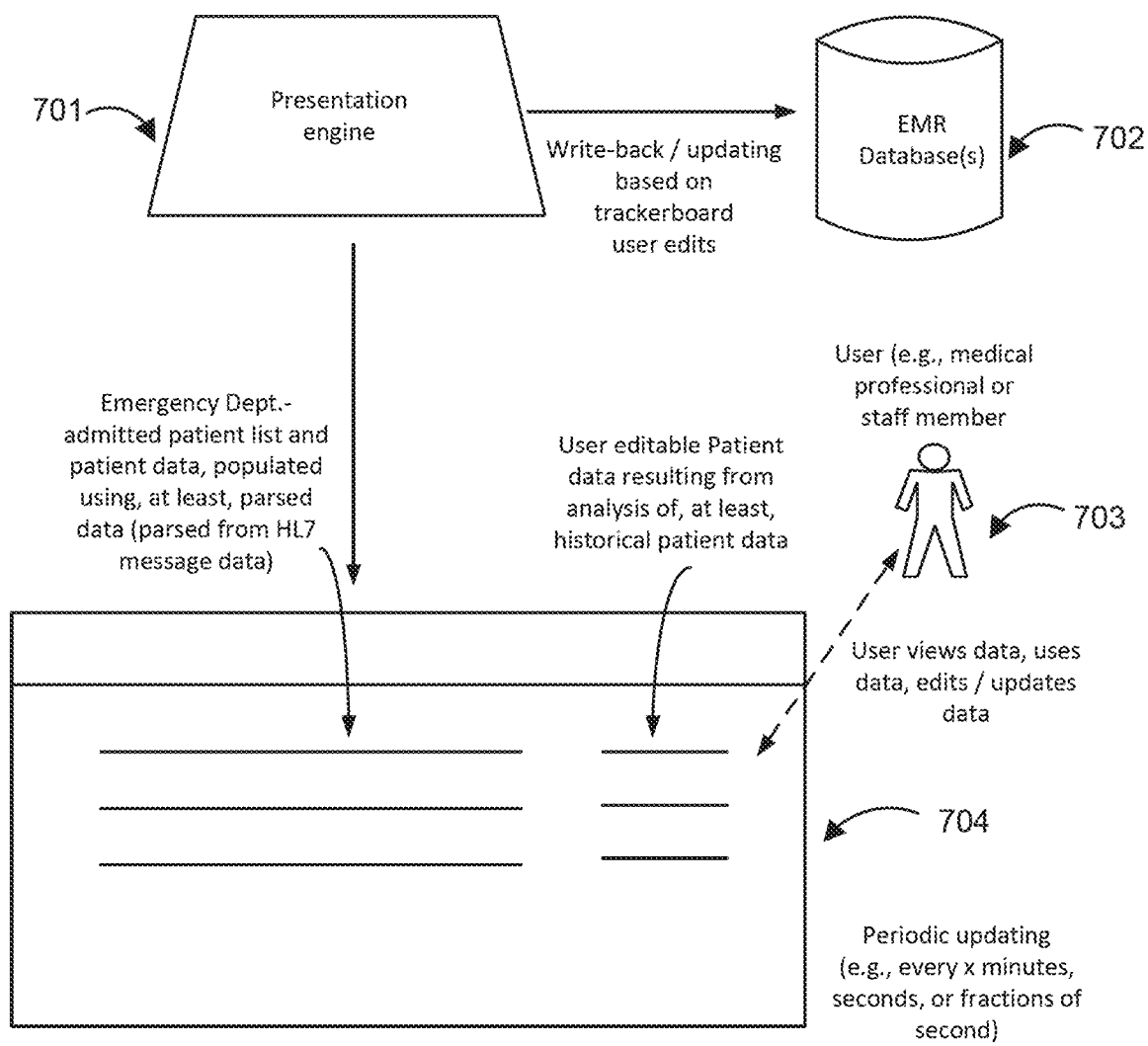
FIG. 7 illustrates a block diagram according to some embodiments of the invention.

FIG. 7. illustrates a block diagram according to some embodiments of the invention, including a presentation engine 701, an EMR database 702 and a GUI-based trackerboard 704. As depicted, the presentation engine 701 is used in generating a GUI-based trackerboard 704. The trackerboard 704 includes a listing of emergency department admitted patients, populated using, at least, parsed data from HL7 message data. The trackerboard 704 further includes additional patient related data for each listed patient, including data resulting from analysis by the presentation engine 701 of, at least, historical patient data in EMR Database(s) 702, and also include at least some user-editable data entered, edited, updated or overwritten by user 703. The user 703 may be a medical professional, staff member or scribe that may view, use and/or edit trackerboard displayed data. The trackerboard 704 is periodically updated, such as on the order of minutes, seconds, or even a fraction of a second. In some embodiments, if user 703 did not save the entered edits, the data entries may be lost. In some embodiments, if user 703 saves the entered edits, the data entries may be written back to the EMR Database(s) 702, or other temporary views or databases.

Figure 8:
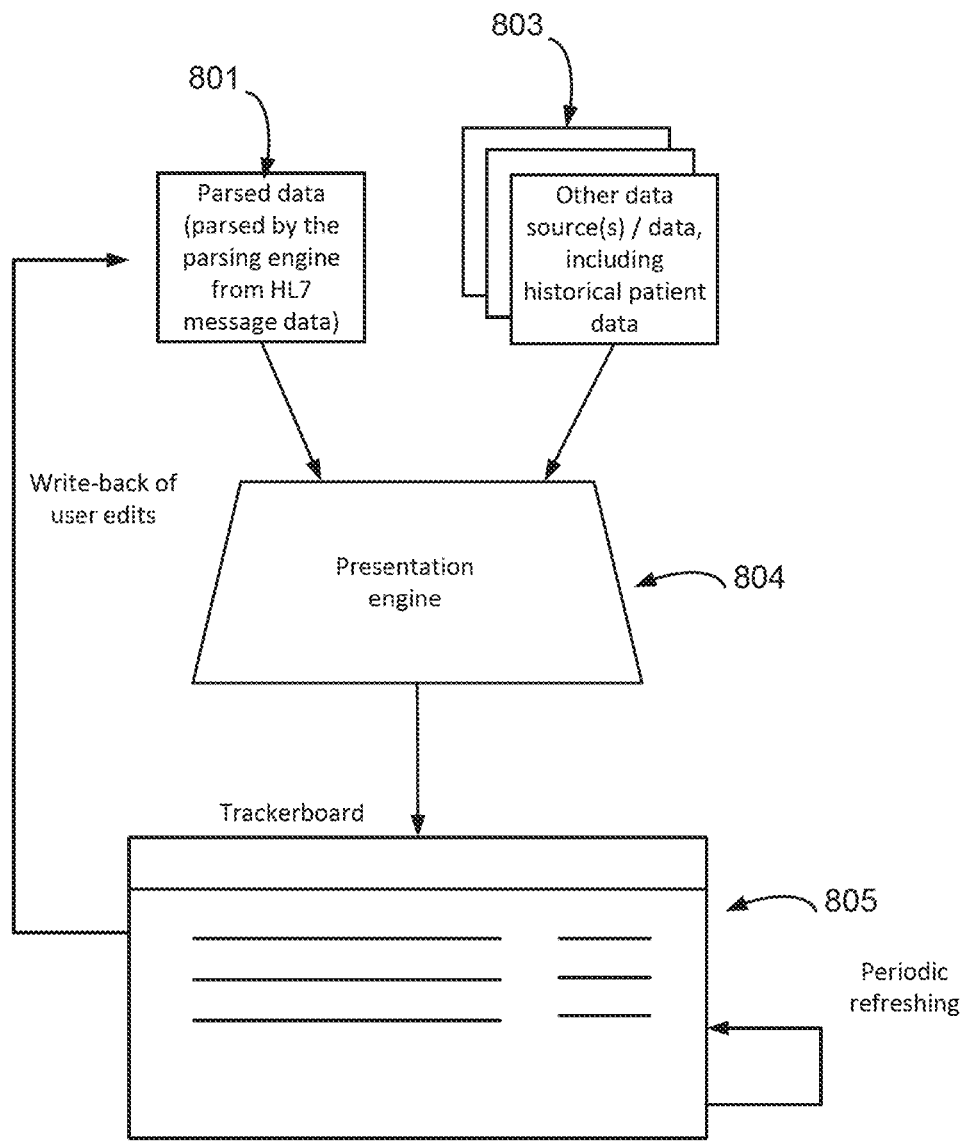
FIG. 8 illustrates a block diagram according to some embodiments of the invention.

FIG. 8 illustrates a block diagram according to some embodiments of the invention, including a presentation engine 804 and a GUI-based trackerboard 805. As depicted, parsed data (parsed by the parsing engine from HL7 message data) 801 and other data 803, including historical patient data, is obtained by and used by the presentation engine in generating trackerboard data and a GUI-based trackerboard display 805, including a list of emergency room admitted patients, and data about those patients. The trackerboard is periodically refreshed. In some embodiments, the trackerboard may be refreshed at regular or irregular intervals or based on some other parameter(s), such as received user edits. User edits are written back and used to update data sources or databases, for example other data 803, as well as in generating updated trackerboard data and trackerboard displays. In some embodiments, parsed patient related data 801 may be used to determine patients currently, or at latest check, admitted to an emergency department of a hospital (or, in other embodiments, other departments, facilities, etc.,) to be listed in the trackerboard display 805. Furthermore, other data, such as historical data may be used and/or analyzed to provide additional patient data associated with listed patients.

Figure 9:
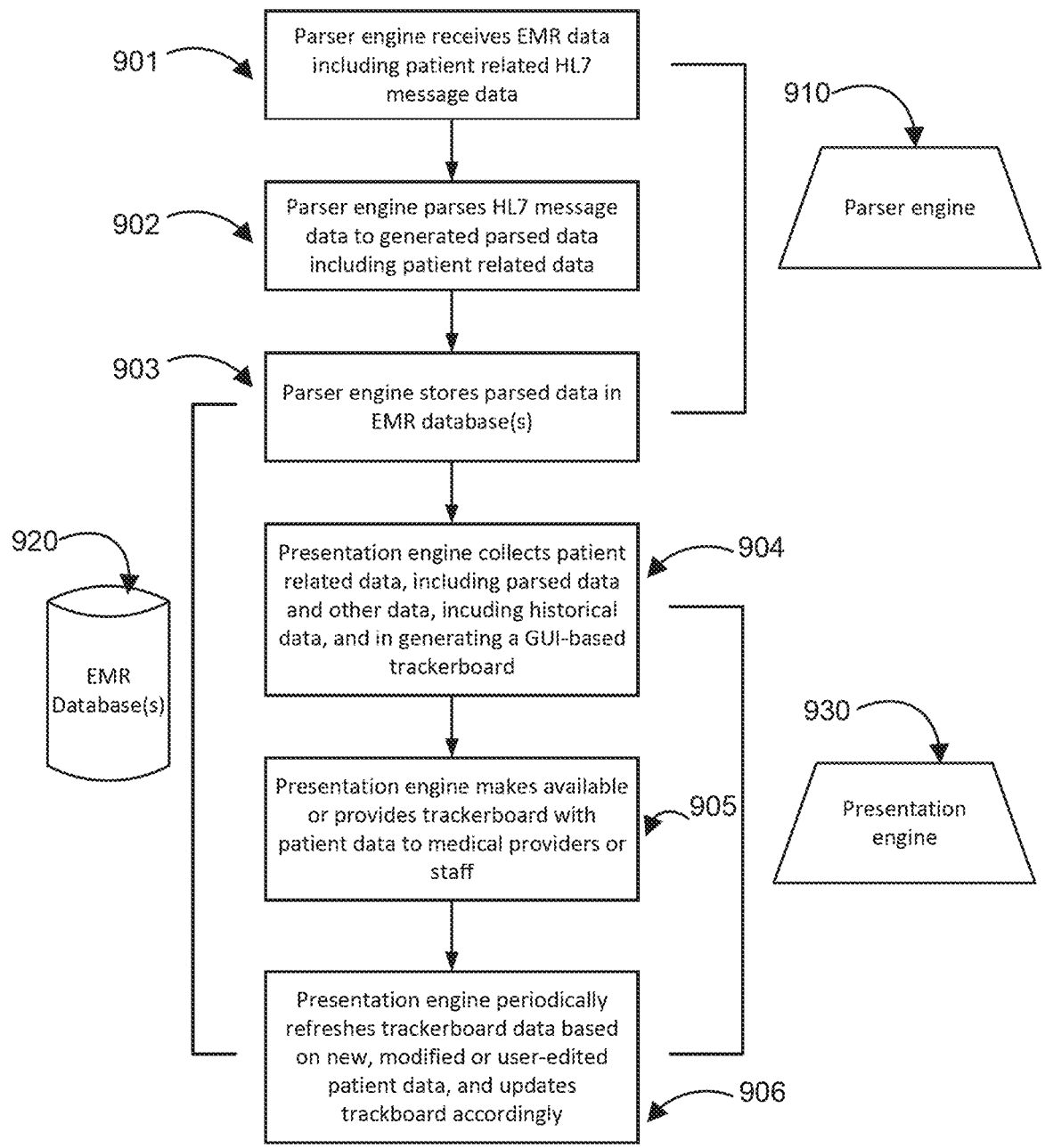
FIG. 9 illustrates a flow diagram of a method according to some embodiments of the invention.

FIG. 9 illustrates a flow diagram of a method according to some embodiments of the invention, including operation of a parser engine 910 and a presentation engine 930. At step 901, a parser engine 910 receives EMR data including patient related HL7 Message data. At step 902, the parser engine parses the HL7 message data to generate parsed data including patient related data. At step 903, the parser engine stores the parsed data in one or more EMR database(s) 920. At step 904, a presentation engine 930 collects patient related data, including parsed data and other data, including historical data, and uses the collected data in generating a GUI-based trackerboard. At step 905, the presentation engine makes available or provides the trackerboard with patient data to medical providers or staff. At step 906, the presentation engine periodically refreshes trackerboard data based on new, modified or user-edited patient data, and updates trackerboard accordingly.

Figure 10:
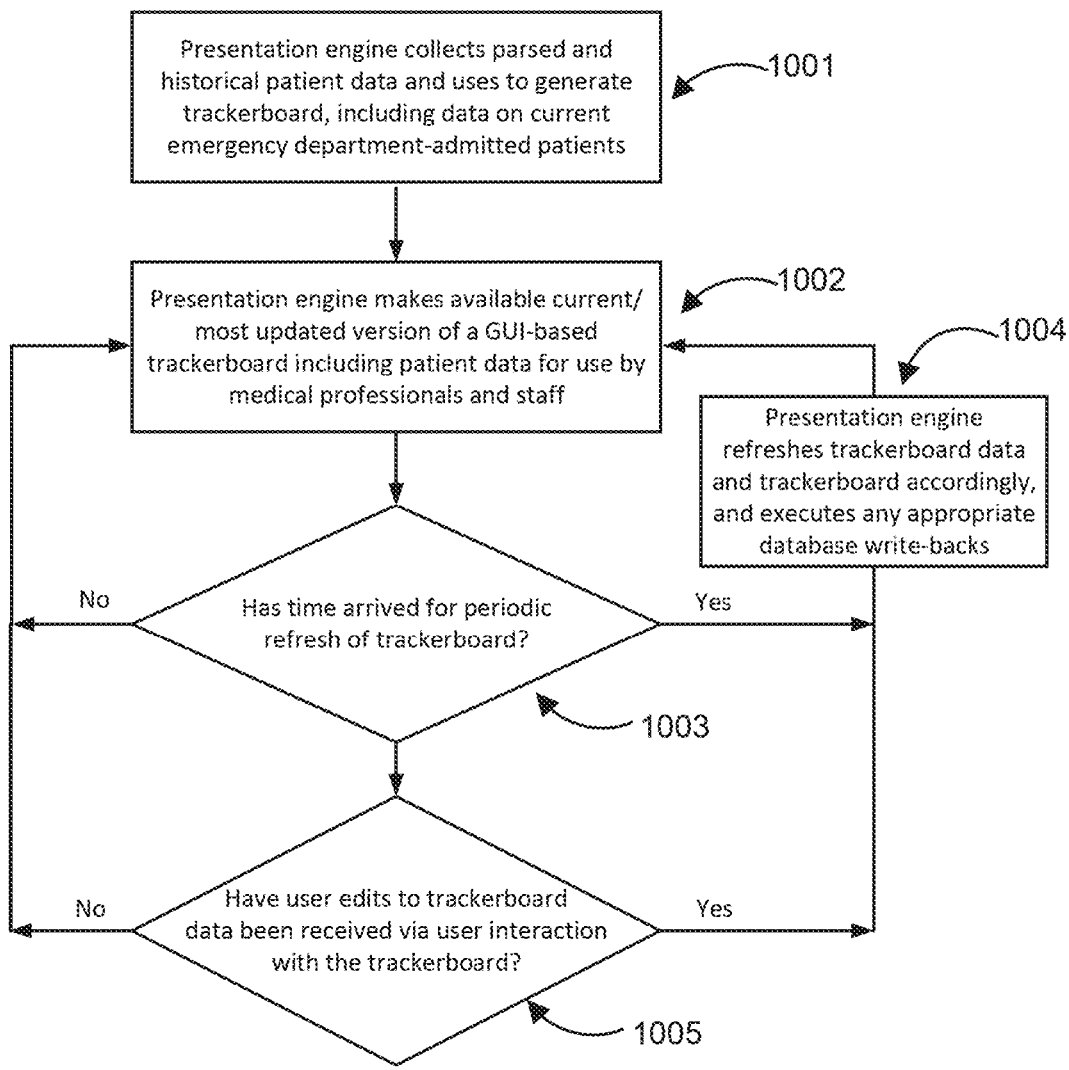
FIG. 10 illustrates a flow diagram of a method according to some embodiments of the invention.

FIG. 10 illustrates a flow diagram of a method according to some embodiments of the invention, including operation of a presentation engine. At step 1001, the presentation engine collects parsed and historical patient data and uses it to generate trackerboard, including data on current (or current at last check) emergency department-admitted patients. At step 1002, the presentation engine makes available current/most updated version of a GUI-based trackerboard including patient data for use by medical professionals and staff. At step 1003, the method queries whether the time has arrived or elapsed to indicate time for periodic refresh/updating of the trackerboard. If not, then the method returns to step 1002. If so, then, at step 1004, the presentation engine refreshes trackerboard data and the trackerboard accordingly. In some embodiments, the method may execute any appropriate database or data store write-backs at this time. Then the method proceeds back to step 1002. At step 1005, the method queries whether user edits to trackerboard data have been received via user interaction with the trackerboard. If not, then the method returns to step 1002. If so, then the method returns to step 1004 and writes back edited data to a data source.

Figure 11:
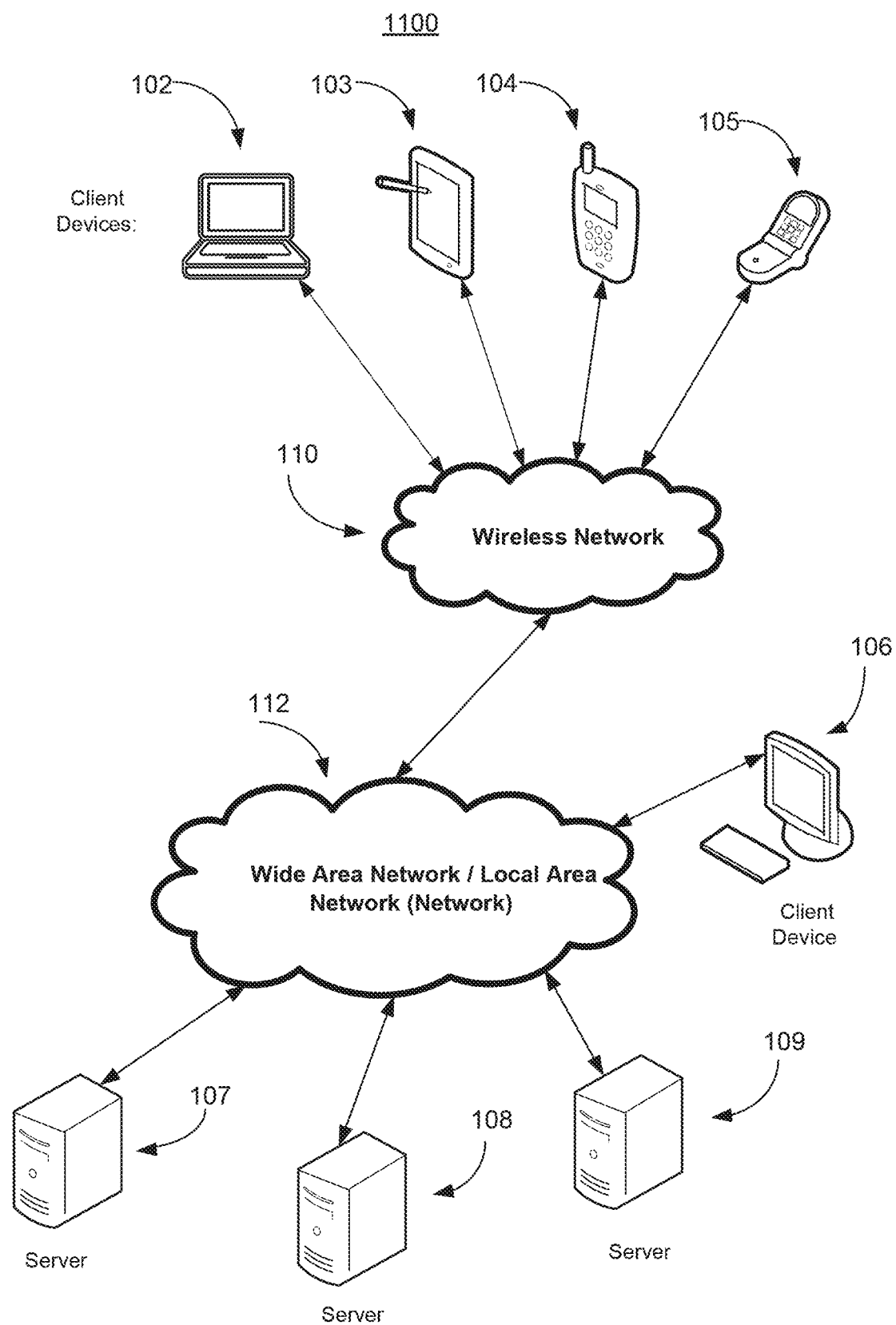
FIG. 11 illustrates a block diagram of a distributed computer system that can implement one or more aspects of an embodiment of the present invention.

FIG. 11 illustrates components of one embodiment of an environment 1100 in which the invention may be practiced. Not all of the components may be required to practice the invention, and variations in the arrangement and type of the components may be made without departing from the spirit or scope of the invention. As shown, the system 1100 includes one or more Local Area Networks ("LANs")/Wide Area Networks ("WANs") 112, one or more wireless networks 110, the Internet, one or more wired or wireless client devices 106, mobile or other wireless client devices 102-106, servers 107-109, and may include or communicate with one or more data stores or databases. Various of the client devices 102-106 may include, for example, desktop computers, laptop computers, set top boxes, tablets, monitors, cell phones, smart phones, devices for interfacing with, or viewing dashboards or analytics relating to, EMR related systems or entities, etc. The servers 107-109 can include, for example, one or more application servers, content servers, search servers, EMR system servers, Mirth-based or other HL7 Messaging servers, Python Flash API-based or other parser engine servers, database servers, database management or SQL servers, etc.

Figure 12:
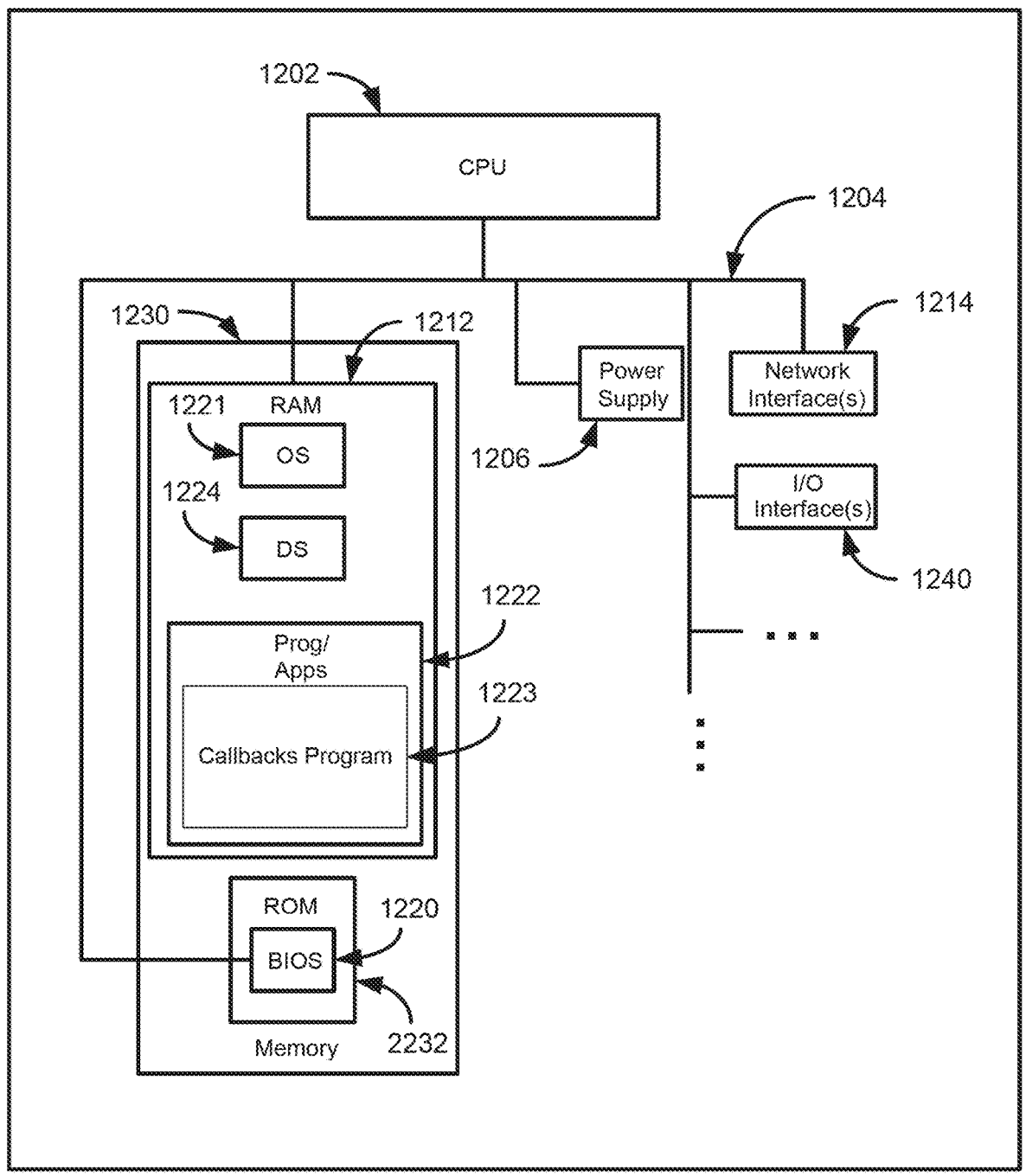
FIG. 12 illustrates a block diagram of an electronic device that can implement one or more aspects of an embodiment of the invention.

FIG. 12 illustrates a block diagram of an electronic device 1200 that can implement one or more aspects of EMR related systems and methods according to embodiments of the invention. Instances of the electronic device 1200 may include servers, e.g., servers 107-109, and client devices, e.g., client devices 102-106. In general, the electronic device 1200 can include a processor/CPU 1202, memory 1230, a power supply 1206, and input/output (I/O) components/devices 1240, e.g., microphones, speakers, displays, touchscreens, keyboards, mice, keypads, microscopes, GPS components, etc., which may be operable, for example, to provide graphical user interfaces, dashboards, etc.

A user may provide input via a touchscreen of an electronic device 1200. A touchscreen may determine whether a user is providing input by, for example, determining whether the user is touching the touchscreen with a part of the user's body such as his or her fingers. The electronic device 1200 can also include a communications bus 1204 that connects the aforementioned elements of the electronic device 1200. Network interfaces 1214 can include a receiver and a transmitter (or transceiver), and one or more antennas for wireless communications.

The processor 1202 can include one or more of any type of processing device, e.g., a Central Processing Unit (CPU), and a Graphics Processing Unit (GPU). Also, for example, the processor can be central processing logic, or other logic, may include hardware, firmware, software, or combinations thereof, to perform one or more functions or actions, or to cause one or more functions or actions from one or more other components. Also, based on a desired application or need, central processing logic, or other logic, may include, for example, a software-controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software.

The memory 1230, which can include Random Access Memory (RAM) 1212 and Read Only Memory (ROM) 1232, can be enabled by one or more of any type of memory device, e.g., a primary (directly accessible by the CPU) or secondary (indirectly accessible by the CPU) storage device (e.g., flash memory, magnetic disk, optical disk, and the like). The ROM 1232 can also include Basic Input/Output System (BIOS) 1220 of the electronic device.

The RAM can include an operating system 1221, data storage 1224, which may include one or more databases, and programs and/or applications 1222 and an EMR program 1223. The EMR program 1223 is intended to broadly include all programming, applications, algorithms, software and other tools necessary to implement or facilitate methods and systems according to embodiments of the invention. Elements of the EMR program 1223 program may exist on a single server computer or be distributed among multiple computers, servers, devices or entities, or sites.

The power supply 1206 contains one or more power components and facilitates supply and management of power to the electronic device 1200.

The input/output components, including Input/Output (I/O) interfaces 1240, can include, for example, any interfaces for facilitating communication between any components of the electronic device 1200, components of external devices (e.g., components of other devices of the network or system 100), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 1240 and the bus 1204 can facilitate communication between components of the electronic device 1200, and in an example can ease processing performed by the processor 1202.

Where the electronic device 1200 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications.

In some embodiments, the trackerboard uses real-time (HL7) data so that providers can view and edit a running list of patients currently in the Emergency Department in real time (as they are coming in and their information is being entered in the EMR system) as well as view analytic data about the patients and capability to update and writeback patient information, for example provider assignments, or diagnoses related information. In some embodiments, HL7 real time data is combined with supplementary or other data. Real time data includes patient encounter details, patient codes, provider, patient, patient insurance and the like. Supplementary or other data includes disease management information, high risk modeling, six-month count, provider daily schedule and the like. In some embodiments, data is written back, including user input via an interface, including provider assignment, or disease management information, or the like. The trackerboard provides a running list of all patients as they enter the hospital and then allows the provider or designee (e.g., scribes) to assign a provider or patient using a drop-down field. In some embodiments, the analytics data includes data analyzed from historical data about the patient, if available, which is not typically available in real time.

In some embodiments, as soon as a patient record is created in the system, when a patient is in the Emergency Department, this information is parsed, patient identifying information is extracted, and the historical databases are queried for historical information about the patient, such as how many times the patient visited the emergency department in the past six months, or another customizable time period, whether the patient previously presented with any particular high risk diagnoses, and perform high risk analysis to determine whether to mark the patient as high risk. In some embodiments, the high risk may be determined via an algorithm and analysis of historical and real time patient data or may be attributed via user input on the trackerboard. In this way, the trackerboard presents real-time information about the patient that is entered when the patient enters the emergency department such as patient information, as well as historical information, which is also presented in real-time relative to data entry of the patient information.

In some embodiments, criteria may be customized to identify patients at a high-risk for a 14-day emergency department (ED) revisit. In one embodiment of the present invention, a logistic regression model approach may be taken to identify patients at high risk for a 14-day revisit by calculating odds of returning. In another embodiment of the present invention, a decision tree model approach may be taken to identify patients at high risk for a 14-day revisit by determining "rules" for returning. Model features for evaluation could be based on, e.g., gender (one or more of, e.g., male/female/transgender/gender non-conforming), age group (e.g., 0-17, 18-25, 26-40, 41-64, 65+), number of ED visits in the last six months, zip code, reason for visit categories (e.g., alcohol-related disorders; chronic kidney disease; hemorrhage during pregnancy, abruptio placenta, placenta previa; immunizations and screening for infectious disease; open wounds of head, neck, trunk; other aftercare; other complications of birth, puerperium affecting management of mother; other disorders of stomach and duodenum; sickle cell anemia; skin and subcutaneous tissue infections).

In some embodiments, customized approaches, methods, techniques, measures, matrices, models, machine learning models, variables, algorithms, classifications, attributes may be used, for example, in high risk assessments. These may include, for example, machine learning techniques, logistic regression techniques, and/or decision tree techniques. For example, in some embodiments, techniques can be used in making predictions or determinations regarding the odds of a patient returning to an emergency department, or returning over some period of time, such as within 14 days, etc., which may, for example, be taken account in a high risk assessment, determination or algorithm. In some embodiments, logistic regression techniques may be used in determining such odds, and decision tree techniques may be used in determining such rules, for example. In some embodiments, the type, quality and/or quantity of available or utilized data, or types of data, may be used to make determinations regarding the assessment itself, such as sensitivity, specificity, precision, accuracy, error, negative prediction value, prevalence, false positives, etc., which may be factored in to risk assessment determinations, for example. Furthermore, data regarding outcomes of predictions may be collected over time and utilized, for example, in assessing and refining the performance of high risk assessment techniques, models, or algorithms themselves, such as, for example, by using such data as feedback for machine learning model, or model features, characteristics, training or refinement. In some embodiments, techniques including use of a confusion matrix, or visualization models, may be used in such performance evaluations, for example.

In some embodiments, various patient data and statistics, individual or group, may be utilized in high risk assessments and techniques. For example, in some embodiments, machine learning techniques may be utilized that use some portion of a set of patient group data as a training set, and some portion as test data, such as 75% training and 25% test, for instance. Categories of conditions may also be taken into account or utilized. For example, data regarding a certain number or proportion of patients in a particular category and the related disposition, or current status, may be required or utilized. In some embodiments, for example, data is utilized to determine categories more or most likely to result in emergency department revisits may be utilized and factored into high risk assessments. For example, in some embodiments, categories may include, for example, alcohol-related disorders, chronic kidney disease, hemorrhage during pregnancy, abruptio placenta, placenta previa, immunizations and screening for infectious disease, open wounds of head, neck, trunk, other aftercare, other complications of birth, puerperium affecting management of mother, other disorders of stomach and duodenum, sickle cell anemia, skin and subcutaneous tissue infections, or others.

In some embodiments, other patient(s) data and category data may also be utilized and factored in, such age or other demographic, medically relating or not medically related, patient or patient category or characteristic data, such a age or age group, zip code or gender, for example.

In some embodiments, the trackerboard uses EMR extracts combined with data from HL7 feeds to create a real-time historical view of patients for a particular site. Using this history in real-time, the trackerboard can analyze the data and create predictions of key metrics such that decision makers can address management needs more rapidly.

Emergency Departments typically track patient lists by keeping a running list of new patients that come in through the emergency department, where providers, beds, and nurses are assigned. However, the conventional way of keeping a running list of patients is problematic in that it merely displays data from an EMR system and database, the EMR system and database is resource heavy to access, nearly impossible to access, display or modify in real-time, in part because the data is typically batch stored in the EMR database, and the data in the EMR system and database is restricted and sometimes not yet stored, available and permitted to be corrected or changed. Conventional systems provide patient lists that are only available within the hospital site on EMR-owned patient lists and there was limited write-back functionality to those, i.e., nurse and provider assignments, bed assignments.

In some embodiments, the trackerboard tool is EMR-agnostic, meaning that it can take HL7 data from any EMR system and display the data for scribes and providers. Thus, there is no need to license a particular EMR system in order to provide this data in real-time thus, the tool is low cost, low maintenance, low resource and scalable to any site using any system or platform. The trackerboard tool also allows scribes and providers to write-back into the tool to flag patients who are high-risk or who should be followed up by case management or care navigators.

In some embodiments, real-time, HL7 data is used to create patient lists that can be used with great flexibility, specifically in this case, to attribute patients or identify high-risk patients in real-time. In some embodiments, the trackerboard provides capability to assign to care navigators, identify patients that came in from certain SNF partners, identify common diagnoses that could be managed in an outpatient setting, etc. In some embodiments, user input to modify, update, enter or overwrite data displayed on the trackerboard can be written back directly to the original source of the data, or written back to an intermediary source of the data and later written back to the EMR system and database. In some embodiments, once the HL7 real-time data as well as user input data matures, it gets written back to the main EMR system.

In some embodiments, the trackerboard tool takes real-time, HL7 admission, discharge, and transfer (ADT) data sent from hospitals and displays them in near (within seconds) real-time in a dashboard. In some embodiments, the trackerboard tool filters patients by ADT status, where the data field indicating discharge is null. The dashboard is typically provisioned to emergency department providers and scribes at the site but can be provisioned to others who need/are allowed access to this data and can be accessed at non-hospital locations, i.e., you do not have to be on hospital premised to view the data. The trackerboard displays patient data (Patient MRN, encounter number, admit date/time stamp, insurance/payer, number of previous emergency department visits) as patients arrive in the hospital emergency department.

In some embodiments, the trackerboard patient list may be run through a High-Risk algorithm that can be customized per hospital site. These "high-risk" patients or patients with additional diagnoses or payer groups, etc. can be customized on the trackerboard tool to identify patients in real-time based on a variety of demographic, revisit, or patient-specific characteristics. These "high-risk" patients may be highlighted based on risk and may be visually distinctive by formatting such as font, color, or a visible marker, quickly visually identifying existence of risk or the type of risk.

In some embodiments, there is an additional column that allows providers or scribes to "attribute" a patient case to a certain provider for callbacks purposes. The reason for this is that the ADT data sent from hospitals is generally completed by Registration staff, without much concern for accuracy in terms of providers who saw the patient. The last column in the trackerboard tool allows users to "re-assign" patient case so that the case is accurately reflected in the provider-specific patient list for callbacks. The tool does not write back in to the EMR. Write-back fields are captured in our SQL database and the business intelligence platform exposes the values written back.

In some embodiments, the trackerboard tool provides reporting or analytics or real-time information to insurance companies by identifying patients by insurance status in real-time at the point of clinical intervention. For example, if an insurance company wants to test an intervention on COPD patients who utilize the emergency department, the trackerboard identifies those patients for the scribes to conduct an intervention. In some embodiments, the trackerboard tool provides federally qualified health centers (FQHC) who want their clinic-enrolled patients to know about appropriate outpatient services. The trackerboard tool may identify patients whose payers are at the FQHC.

In some embodiments, the trackerboard tool consists of a desktop and mobile version. Both present provider-specific patient lists, containing patient name, date of service, insurance, any risk status (e.g., multiple emergency department visits over last 6 months), phone number, and drop-down fields indicating status of trackerboard (i.e., spoke to patient, no answer/left message, etc.). The tool has several modes of populating the patient list: real-time data (HL7), historical data or analytics data and through manual entry. With real-time data, programming logic pulls data directly from databases to pre-populate provider-specific lists. With the manual entry mode, providers or designees (e.g., scribes) enter in patient information into the trackerboard entry form that then pulls that information into provider-specific lists. With historical or analytics data, the programing logic pulls data from a batch or historical database, as well as performs analytics on the data. The tool logs completed encounters and provides summary statistics on completed encounters over time.

In some embodiments, the trackerboard uses real-time (HL7) data and providers can add patients to their specific list. The trackerboard provides a running list of all patients as they enter the hospital and then allows the provider or designee (e.g., scribes) to assign a patient to their list using a drop-down field. The tool also allows provider attribution through a drop-down list.

In some embodiments, the trackerboard tool is provisioned to medical providers (physicians, advanced providers), scribes, and on-site administrators (aka Practice Administrators or Program Managers).

In some embodiments, the trackerboard tool is built leveraging a business intelligence platform and multiple layers of security. Users are provisioned access to the desktop platform, and once provisioned, will display as a tile on the medical application portal. The trackerboard tool is further secured at the business intelligence platform layer, restricting user access to tools for which they have been provisioned to and which are relevant to their workflows. Lastly, the tools have row level security in place which restricts data access based on a user's credentialed sites/locations and roles at those respective sites/locations. Access is maintained and audited by a centralized medical security administration team which is responsible for provisioning, reviewing, and terminating access to medical applications.

In some embodiments, the trackerboard mobile application is built on a business intelligence platform such as the MicroStrategy platform and is compatible with both Android & iOS devices. Users are provisioned to the mobile application by centralized IT security administration team via an Okta group. Provisioning into this master group then prompts Usher Security Network to issue an electronic badge to the user—allowing users to access the mobile applications via standard mobile authentication methods (i.e. pin codes, biometrics, etc.).

In some embodiments, the access is controlled centrally through a single sign-on (SSO) process. Users may access the trackerboard tool through hospital computers, personal computers, or personal mobile devices. Only authorized providers and staff can the trackerboard tool.

In some embodiments, the HL7 data is transmitted to RCM for billing purposes through a secure VPN. With hospital approval, that same feed is used to populate information into the trackerboard tool. Specifically, the tool may use fields such as Patient Name, Discharge Date, MRN, Encounter #, Payer type, Contact Phone, Reason for visit, Age/DOB, Diagnosis (for disease management version), and the like.

In some embodiments, the data from the trackerboard tool is stored on intermediary servers which are secured by the centralized IT security administration. Intermediary data is co-located in a SOC2 certified data center and follows all standard at-rest and in-transit encryption.

In some embodiments, the trackerboard tool leverages a variety of different data sources that enables us to offer a provider-centric solution to current visit management. The base layer of information for the trackerboard tool comes from real time data that is transferred via HL7 messages from the hospital site. This data is transferred from the hospital site directly to RCM and then sent over to a parsing engine that parses, appropriately inserts, and stores the data into a real-time data warehouse. The HL7 parsing engine allows for consumption of data from any hospital system or site regardless of the EMR system. Building an EMR agnostic solution positions trackerboard tool for deployment to any hospital site across the country and multiple specialties (i.e., not just emergency department).

In some embodiments, the real time feed is further enriched with other historical or batch data sources, including, billing data to calculate a patient's total visits over the course of 6 months, a high-risk algorithm catered to each site to account for patients with a high likelihood of revisit and provider scheduling data for attribution of patients and added layers of security. For sites leveraging the trackerboard tool for Disease Management, the data is further enriched with either billing data to identify patients with specific diagnosis codes, or a direct load of a flat file provided by the hospital from the EMR system. The list of diagnosis codes to flag patients with specific diseases are hospital specific and allows for maximum flexibility.

The registration process varies greatly between sites and can lead to incomplete or inaccurate data in the HL7 messages. The hospital registration process does not typically accurately capture attending provider. In some embodiments, a list of patients is displayed to a user as the patients are entering (and registering with) the emergency department in real-time. User may update respective patient record with appropriate assigned provider, or flags for Disease Management (CHF/COPD). In some embodiments, the trackerboard tool allows scribes or providers to manually override the provider attribution of patient records with a drop-down list of patients scheduled at the site. The trackerboard tool is bi-directional which enables further accuracy of patient lists. The trackerboard tool enriches data and provides for increased accuracy, solving the painstaking manual process of completing and tracking patient encounters.

In some embodiments, the trackerboard tool provides a desktop and mobile application that dynamically populates patient lists for providers, provides summary data on the patient and visit and even integrates with dialing functions on the mobile or desktop for quick follow up phone calls to patients, masking a provider's cell phone number as a hospital site's number.

In some embodiments, patients are displayed to the hospital leadership for review and reporting, including for example insured lives analysis, as well as a provider's compliance with various requirements, ultimately leading to an improved patient experience, reduced likelihood of revisit & higher patient satisfaction results.

According to one embodiment, a computer-implemented system is provided for use with Electronic Medical Records (EMRs), the system comprising a parser engine configured to receive, in real time or near real time relative to entry of EMR data into an EMR system, Health Level 7 (HL7) messages including the EMR data, and using parsing logic, parse, in real time or near real time relative to entry of the EMR data, the HL7 messages to identify and extract specified EMR data therefrom, a database configured to, in real time or near real time relative to entry of the EMR data, receive and store parsed data comprising the extracted specified EMR data, a presentation engine configured to display a trackerboard, wherein the trackerboard includes a graphical user interface that presents collected patient data, and wherein the collected patient data comprises a list of patients currently admitted to an emergency department of a medical facility or hospital, wherein the list of patients is determined using patient data obtained from the parsed data, and analytic EMR data relating to each patient in the list of patients, wherein the analytic EMR data is obtained from analysis of, at least, obtained historical EMR data relating to each of the patients, wherein the collected patient data is periodically refreshed based on the parsed data and edits received via user interaction with the trackerboard.

According to one embodiment, a computer-implemented method is provided for use with Electronic Medical Records (EMRs), the method comprising receiving, by a parser engine, in real time or near real time relative to entry of EMR data into an EMR system, Health Level 7 (HL7) messages including the EMR data, and using parsing logic, parsing, by the parser engine, in real time or near real time relative to entry of the EMR data, the HL7 messages to identify and extract specified EMR data therefrom, receiving and storing by a database parsed data comprising the extracted specified EMR data, in real time or near real time relative to entry of the EMR data, displaying a trackerboard by a presentation engine, wherein the trackerboard includes a graphical user interface that presents collected patient data, and wherein the collected patient data comprises a list of patients currently admitted to an emergency department of a medical facility or hospital, wherein the list of patients is determined using patient data obtained from the parsed data, and analytic EMR data relating to each patient in the list of patients, wherein the analytic EMR data is obtained from analysis of, at least, obtained historical EMR data relating to each of the patients, wherein the collected patient data is periodically refreshed based on the parsed data and edits received via user interaction with the trackerboard.

According to one embodiment, a non-transitory computer readable medium or media is provided containing instructions for executing a method for use with Electronic Medical Records (EMRs), the method comprising receiving, by a parser engine, in real time or near real time relative to entry of EMR data into an EMR system, Health Level 7 (HL7) messages including the EMR data, and using parsing logic, parsing, by the parser engine, in real time or near real time relative to entry of the EMR data, the HL7 messages to identify and extract specified EMR data therefrom, receiving and storing by a database parsed data comprising the extracted specified EMR data, in real time or near real time relative to entry of the EMR data, displaying a trackerboard by a presentation engine, wherein the trackerboard includes a graphical user interface that presents collected patient data, and wherein the collected patient data comprises a list of patients currently admitted to an emergency department of a medical facility or hospital, wherein the list of patients is determined using patient data obtained from the parsed data, and analytic EMR data relating to each patient in the list of patients, wherein the analytic EMR data is obtained from analysis of, at least, obtained historical EMR data relating to each of the patients, wherein the collected patient data is periodically refreshed based on the parsed data and edits received via user interaction with the trackerboard.

According to one embodiment, a computer-implemented system is provided for use with Electronic Medical Records (EMRs), the system comprising a parser engine configured to receive, in real time or near real time relative to entry of EMR data into an EMR system, Health Level 7 (HL7) messages including the EMR data, and using parsing logic, parse, in real time or near real time relative to entry of the EMR data, the HL7 messages to identify and extract specified EMR data therefrom, a database configured to, in real time or near real time relative to entry of the EMR data, receive and store parsed data comprising the extracted specified EMR data, a presentation engine configured to display a trackerboard, wherein the trackerboard includes a graphical user interface that presents collected patient data, and wherein the collected patient data comprises a list of patients currently admitted to an emergency department of a medical facility or hospital, wherein the list of patients is determined using patient data obtained from the parsed data, and analytic EMR data relating to each patient in the list of patients, wherein the analytic EMR data is obtained from analysis of, at least, obtained historical EMR data relating to each of the patients, wherein the collected patient data is periodically refreshed based on the parsed data and edits received via user interaction with the trackerboard.

In some embodiments, the graphical user interface provides writeback functionality for updates, edits, or overwrites to collected patient data. In some embodiments, patients are identified by insurance status in real time or near real time relative to entry of the EMR data. In some embodiments, the patient list is filtered by at least one of admission status and discharge status. In some embodiments, the trackerboard displays or enables display of at least a portion of the list of patients and analytic EMR data. In some embodiments, the trackerboard is updated by refreshing at least one of the list of patients and the analytic EMR data in real time or near real time relative to entry of the EMR data. In some embodiments, the analytic EMR data includes historical EMR data.

In some embodiments, the parser engine is implemented utilizing Python Flash API. In some embodiments, the HL7 messages are received by the parser engine and originate from multiple EMR systems. In some embodiments, a relational database management system (RDBMS), utilizes Structured Query Language (SQL) and a temporal table structure for storage of both chronologically tracked historical EMR data and current EMR data. In some embodiments, the presentation engine utilizes one or more machine learning models.

In some embodiments, a relational database management system (RDBMS), utilizes Structured Query Language (SQL), configured to manage the database system, wherein the RDBMS utilizes a temporal table structure for storage of, per patient, both chronologically tracked historical EMR data and current EMR data, and wherein both chronologically tracked historical EMR data and current EMR data are utilized in analysis to determine the analytic EMR data with chronological aspects. In some embodiments, a relational database management system (RDBMS) utilizes Structured Query Language (SQL), configured to manage the database, wherein the RDBMS utilizes a set of tables that are designed to optimize or speed determination of analytical result data.

In some embodiments, the parser logic comprises logic to logically divide HL7 messages into segments. In some embodiments, the parser logic comprises logic to cause parsing of only HL7 messages that are determined to include one or more segments needed to determine specific analytic results data. In some embodiments, the parser logic comprises logic to determine efficient or optimal storage of extracted EMR data across one or more tables of the database. In some embodiments, the parser logic comprises logic to, for efficiency, avoid extraction of EMR data already extracted from a previous HL7 message. In some embodiments, the parser engine comprises logic to identify particular segments within the HL7 messages and logic to identify particular fields within the particular segments.

According to one embodiment, a computer-implemented method is provided for use with Electronic Medical Records (EMRs), the method comprising receiving, by a parser engine, in real time or near real time relative to entry of EMR data into an EMR system, Health Level 7 (HL7) messages including the EMR data, and using parsing logic, parsing, by the parser engine, in real time or near real time relative to entry of the EMR data, the HL7 messages to identify and extract specified EMR data therefrom, receiving and storing by a database parsed data comprising the extracted specified EMR data, in real time or near real time relative to entry of the EMR data, displaying a trackerboard by a presentation engine, wherein the trackerboard includes a graphical user interface that presents collected patient data, and wherein the collected patient data comprises a list of patients currently admitted to an emergency department of a medical facility or hospital, wherein the list of patients is determined using patient data obtained from the parsed data, and analytic EMR data relating to each patient in the list of patients, wherein the analytic EMR data is obtained from analysis of, at least, obtained historical EMR data relating to each of the patients, wherein the collected patient data is periodically refreshed based on the parsed data and edits received via user interaction with the trackerboard.

According to one embodiment, a non-transitory computer readable medium or media is provided containing instructions for executing a method for use with Electronic Medical Records (EMRs), the method comprising receiving, by a parser engine, in real time or near real time relative to entry of EMR data into an EMR system, Health Level 7 (HL7) messages including the EMR data, and using parsing logic, parsing, by the parser engine, in real time or near real time relative to entry of the EMR data, the HL7 messages to identify and extract specified EMR data therefrom, receiving and storing by a database parsed data comprising the extracted specified EMR data, in real time or near real time relative to entry of the EMR data, displaying a trackerboard by a presentation engine, wherein the trackerboard includes a graphical user interface that presents collected patient data, and wherein the collected patient data comprises a list of patients currently admitted to an emergency department of a medical facility or hospital, wherein the list of patients is determined using patient data obtained from the parsed data, and analytic EMR data relating to each patient in the list of patients, wherein the analytic EMR data is obtained from analysis of, at least, obtained historical EMR data relating to each of the patients, wherein the collected patient data is periodically refreshed based on the parsed data and edits received via user interaction with the trackerboard.

According to one embodiment, a method for providing an interface configured to run on a user device is provided, the method comprising extracting patient detail batch information at a pre-defined time interval for one or more past patients from an electronic medical records (EMR) database or other patient information database into a medical activity tracking batch database, constructing a real-time database from streams of real-time Health Level 7 (HL7) data, wherein at least one stream of real-time HL7 data is associated with the at least one patient in a current or recent medical encounter and at least one stream of real-time HL7 data comprises daily schedule information associating the at least one clinician with the at least one patient, creating a database view table comprising patient detail batch information and real-time HL7 data for the at least one patient and daily schedule information for the at least one clinician, generating a user interface configured for display at the user device including at least a part of the database view table, and receiving and recording in the database view table, medical information from the at least one user through the user interface displayed at the user device.

In some embodiments, the method further comprises updating the at least one patient or the at least one clinician via the user interface. In some embodiments, the at least one high-risk patient is flagged using a machine learning model applied to patient detail batch information retrieved at a pre-defined time interval for one or more past patients from an electronic medical records (EMR) database or other patient information database.

In some embodiments, the method further comprises generating a user interface enabling the at least one clinician to manually update an assignment of the at least one clinician to the at least one patient. In some embodiments, the method further comprises generating a user interface enabling at least one medical site director to edit one or more callback target or provider attribution configurations.

According to one embodiment, a computer-implemented system for use with Electronic Medical Record (EMR) data associated with one or more patients is provided, the system comprising a parser engine configured to receive, in real time or near real time relative to entry of EMR data into an EMR system, Health Level 7 (HL7) messages including the EMR data, and using parsing logic, parse, in real time or near real time relative to entry of the EMR data, the HL7 messages to identify and extract specified EMR data therefrom. The system further comprises a database system, comprising one or more databases, configured to, in real time or near real time relative to entry of the EMR data, receive and store the extracted specified EMR data, an analytics and presentation engine configured to display in real time or near real time, a list of patients, wherein the patient list comprises a graphical user interface that presents specified analytic results data determined from analysis of particular EMR data in real time or near real time relative to entry of the EMR data. The specified analytic results data comprises, a list of one or more patients currently or recently admitted to an emergency department of a medical facility or hospital, wherein the list of patients is determined using the extracted specified EMR data, and analytic EMR data relating to each patient in the list of patients, wherein the analytic EMR data is obtained from analysis of the extracted specified EMR data, wherein the EMR data is refreshed based on interaction of at least one user with the patient list.

In some embodiments, the patient list includes at least one high-risk patient, wherein the at least one high-risk patient is flagged using a machine learning model applied to patient detail batch information retrieved at a pre-defined time interval for one or more past patients from an electronic medical records (EMR) database or other patient information database. In some embodiments, the system further comprises one or more alternative patient databases comprises a billing database or a scheduling database.

In some embodiments, the patient list includes at least one high-risk patient, wherein the at least one high-risk patient is determined by calculating a risk of revisit of the at least one high-risk patient to a hospital emergency department based on analytic EMR data or patient data from one or more alternative patient databases.

In some embodiments, the graphical user interface further comprises an interface configured to enable the at least one clinician to manually update an assignment of the at least one clinician to the at least one patient.

In some embodiments, the graphical user interface further comprises an interface configured to enable at least one medical site director to edit one or more callback target or provider attribution configurations.

According to one embodiment, a computer-related product is provided comprising a non-transitory computer readable medium storing instructions for providing an interface configured to run on a user device, wherein the instructions upon execution by a processor perform the steps of extracting patient detail batch information at a pre-defined time interval for one or more past patients from an electronic medical records (EMR) database or other patient information database into a medical activity tracking batch database, constructing a real-time database from streams of real-time Health Level 7 (HL7) clinical administrative data, wherein at least one stream of real-time HL7 clinical administrative data is associated with the at least one patient in a current or recent medical encounter and at least one stream of real-time HL7 data comprises daily schedule information associating the at least one clinician with the at least one patient, creating a database view table comprising patient detail batch information and real-time HL7 data for the at least one patient and daily schedule information for the at least one clinician, generating a user interface configured for display at the user device to enable the at least one clinician to contact the at least one patient via the user device, and receiving and recording in the database view table, medical follow-up disposition information from the at least one clinician through the user interface displayed at the user device.

In some embodiments, the at least one high-risk patient is flagged by using a machine learning model applied to patient detail batch information retrieved at a pre-defined time interval for one or more past patients from an electronic medical records (EMR) database or other patient information database.

In some embodiments, the computer-related product further comprises generating a user interface enabling the at least one clinician to manually update an assignment of the at least one clinician to the at least one patient.

In some embodiments, the computer-related product further comprises generating a user interface enabling at least one medical site director to edit one or more callback target or provider attribution configurations.

Any computing device capable of sending, receiving, and processing data over a wired and/or a wireless network may act as a server, such as in facilitating aspects of implementations of EMR related systems and methods according to embodiments of the invention. Devices acting as a server may include devices such as dedicated rack-mounted servers, desktop computers, laptop computers, set top boxes, integrated devices combining one or more of the preceding devices, etc.

Servers may vary widely in configuration and capabilities, but they generally include one or more central processing units, memory, mass data storage, a power supply, wired or wireless network interfaces, input/output interfaces, and an operating system such as Windows Server, Mac OS X, Unix, Linux, FreeBSD, and the like.

A server may include, for example, a device that is configured, or includes a configuration, to provide data or content via one or more networks to another device, such as in facilitating aspects of an example EMR systems and methods according to embodiments of the invention. One or more servers may, for example, be used in hosting a Web site, such as the web site www.microsoft.com. One or more servers may host a variety of sites, such as, for example, business sites, informational sites, social networking sites, educational sites, wilds, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of EMR systems and methods according to embodiments of the invention. Content may include, for example, text, images, audio, video, and the like.

In example aspects of EMR systems and methods according to embodiments of the invention, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, monitors, sensor-equipped devices, laptop computers, set top boxes, wearable computers, integrated devices combining one or more of the preceding devices, and the like.

Client devices may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, GPS or other location-aware capability, and a 2D or 3D touch-sensitive color screen on which both text and graphics may be displayed.

Client devices, such as client devices, for example, as may be used in example EMR systems and methods according to embodiments of the invention, may run a variety of operating systems, including personal computer operating systems such as Windows, iOS or Linux, and mobile operating systems such as iOS, Android, Windows Mobile, and the like. Client devices may be used to run one or more applications that are configured to send or receive data from another computing device. Client applications may provide and receive textual content, multimedia information, and the like. Client applications may perform actions such as viewing or interacting with analytics or dashboards, interacting with medical, patient-related, hospital or medical facility-related, EMR or EMR-related entities or systems, browsing webpages, using a web search engine, interacting with various apps stored on a smart phone, sending and receiving messages via email, SMS, or MMS, playing games, receiving advertising, watching locally stored or streamed video, or participating in social networks.

In example aspects of EMR systems and methods according to embodiments of the invention, one or more networks, such as networks 1010 or 1012, for example, may couple servers and client devices with other computing devices, including through wireless network to client devices. A network may be enabled to employ any form of computer readable media for communicating information from one electronic device to another. A network may include the Internet in addition to Local Area Networks (LANs), Wide Area Networks (WANs), direct connections, such as through a Universal Serial Bus (USB) port, other forms of computer-readable media, or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 1010, as in example EMR systems and methods according to embodiments of the invention, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, Appletalk, and the like. Versions of the Internet Protocol include IPv4 and IPv6. The Internet includes local area networks (LANs), Wide Area Networks (WANs), wireless networks, and long haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in example EMR systems and methods according to embodiments of the invention, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's Web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

One embodiment of the present invention includes systems, methods, and a non-transitory computer readable storage medium or media tangibly storing computer program logic capable of being executed by a computer processor.

While the present invention has been particularly described with respect to the illustrated embodiments, it will be appreciated that various alterations, modifications and adaptations may be made based on the present disclosure and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the appended claims.

What is claimed is:

1. A computer-implemented system for use with Electronic Medical Records (EMRs), the system comprising:
   a Health Level 7 (HL7) messaging engine configured to:
      receive, in real time or near real time, EMR data entered into at least one EMR system by a medical professional, staff member, or system;
   a parser engine configured to:
      receive, in real time or near real time relative to entry of EMR data into an EMR system, Health Level 7 (HL7) messages including the EMR data from the HL7 messaging engine; and
      using parsing logic, parse, in real time or near real time relative to entry of the EMR data, the HL7 messages to identify and extract specified EMR data therefrom, wherein the specified EMR data comprises patient clinical data obtained during a current medical visit, the patient clinical data comprising one or more of a health-related patient complaint, lab tests ordered for diagnosing a patient, and collected patient vitals;
   a database configured to, in real time or near real time relative to entry of the EMR data, receive and store parsed HL7 data comprising the extracted specified EMR data;
   a presentation engine configured to display a trackerboard, wherein the trackerboard includes a graphical user interface that presents collected patient data, and wherein the trackerboard is configured to override the stored parsed HL7 data in the database, via user interaction with the graphical user interface, and wherein the interaction includes adding, removing, editing or updating the collected patient data, and wherein the collected patient data comprises:
      a list of one or more patients currently admitted to an emergency department of a medical facility or hospital, wherein the list of one or more patients is determined using patient data obtained from the parsed HL7 data; and
      analytic EMR data relating to one or more patients in the list of patients, wherein the analytic EMR data includes a risk assessment of emergency department (ED) visit by the one or more patients occurring within a specified time period, and is obtained from analysis of, at least, the specified EMR data relating to the one or more patients, and historical and chronologically tracked demographic and EMR data relating to information of a plurality of patients relevant to at least one particular analytical use case related to the current medical visit;
   wherein the trackerboard overrides the stored parsed HL7 data in the database based on the user interaction with the graphical user interface, and
   wherein the collected patient data, including the analytic EMR data, is periodically refreshed based on the parsed HL7 data and overrides received via user interaction with the trackerboard.

2. The system of claim 1, wherein the graphical user interface provides writeback functionality for updates, edits, or overwrites to collected patient data.

3. The system of claim 1, further comprising identifying patients by insurance status in real time or near real time relative to entry of the EMR data.

4. The system of claim 1, further comprising filtering the patient list by at least one of admission status and discharge status.

5. The system of claim 1, wherein displaying the trackerboard comprises displaying or enabling display of at least a portion of the list of patients and analytic EMR data.

6. The system of claim 1, further comprising updating the trackerboard by refreshing at least one of the list of patients and the analytic EMR data in real time or near real time relative to entry of the EMR data.

7. The system of claim 1, wherein the analytic EMR data includes historical EMR data.

8. The system of claim 1, wherein the parser engine is implemented utilizing Python Flash API.

9. The system of claim 1, wherein the HL7 messages received by the parser engine originate from multiple EMR systems.

10. The system of claim 1, comprising:
    a relational database management system (RDBMS), utilizing Structured Query Language (SQL) and a temporal table structure for storage of both chronologically tracked historical EMR data and current EMR data.

11. The system of claim 1, wherein the presentation engine utilizes one or more machine learning models.

12. The system of claim 1, comprising:
    a relational database management system (RDBMS), utilizing Structured Query Language (SQL), configured to manage the database system;
    wherein the RDBMS utilizes a temporal table structure for storage of, per patient, both chronologically tracked historical EMR data and current EMR data; and
    wherein both chronologically tracked historical EMR data and current EMR data are utilized in analysis to determine the analytic EMR data with chronological aspects.

13. The system of claim 1, comprising:
a relational database management system (RDBMS), utilizing Structured Query Language (SQL), configured to manage the database;
wherein the RDBMS utilizes a set of tables that are designed to optimize or speed determination of analytical result data.

14. The system of claim 1, wherein the parser logic comprises:
logic to logically divide HL7 messages into segments.

15. The system of claim 1, wherein the parser logic comprises:
logic to cause parsing of only HL7 messages that are determined to include one or more segments needed to determine specific analytic results data.

16. The system of claim 1, wherein the parser logic comprises:
logic to determine efficient or optimal storage of extracted EMR data across one or more tables of the database.

17. The system of claim 1, wherein the parser logic comprises:
logic to, for efficiency, avoid extraction of EMR data already extracted from a previous HL7 message.

18. The system of claim 1, wherein the parser engine comprises logic to identify particular segments within the HL7 messages and logic to identify particular fields within the particular segments.

19. A computer-implemented method for use with Electronic Medical Records (EMRs), the method comprising:
receiving, by a Health Level 7 (HL7) messaging engine, in real time or near real time, EMR data entered into at least one EMR system by a medical professional, staff member, or system;
receiving, by a parser engine, in real time or near real time relative to entry of EMR data into an EMR system, Health Level 7 (HL7) messages including the EMR data from the HL7 messaging engine;
using parsing logic, parsing, by the parser engine, in real time or near real time relative to entry of the EMR data, the HL7 messages to identify and extract specified EMR data therefrom, wherein the specified EMR data comprises patient clinical data obtained during a current medical visit, the patient clinical data comprising one or more of a health-related patient complaint, lab tests ordered for diagnosing a patient, and collected patient vitals;
receiving and storing by a database parsed HL7 data comprising the extracted specified EMR data, in real time or near real time relative to entry of the EMR data;
displaying a trackerboard by a presentation engine, wherein the trackerboard includes a graphical user interface that presents collected patient data, and wherein the collected patient data comprises:
a list of one or more patients currently admitted to an emergency department of a medical facility or hospital, wherein the list of one or more patients is determined using patient data obtained from the parsed HL7 data; and
analytic EMR data relating to one or more patients in the list of patients, wherein the analytic EMR data includes a risk assessment of emergency department (ED) visit by the one or more patients occurring within a specified time period, and is obtained from analysis of, at least, the specified EMR data relating to the one or more patients, and historical and chronologically tracked demographic and EMR data relating to information of a plurality of patients relevant to at least one particular analytical use case related to the current medical visit;
wherein the trackerboard overrides the stored parsed HL7 data in the database based on the user interaction with the graphical user interface, and
wherein the collected patient data, including the analytical EMR data, is periodically refreshed based on the parsed HL7 data and overrides received via user interaction with the trackerboard; and
overriding, by the trackerboard, the stored parsed HL7 data in the database, via user interaction with the graphical user interface, and wherein the interaction includes adding, removing, editing or updating the collected patient data.

20. A non-transitory computer readable medium or media containing instructions for executing a method for use with Electronic Medical Records (EMRs), the method comprising:
receiving, by a Health Level 7 (HL7) messaging engine, in real time or near real time, EMR data entered into at least one EMR system by a medical professional, staff member, or system;
receiving, by a parser engine, in real time or near real time relative to entry of EMR data into an EMR system, Health Level 7 (HL7) messages including the EMR data from the HL7 messaging engine;
using parsing logic, parsing, by the parser engine, in real time or near real time relative to entry of the EMR data, the HL7 messages to identify and extract specified EMR data therefrom, wherein the specified EMR data comprises patient clinical data obtained during a current medical visit, the patient clinical data comprising one or more of a health-related patient complaint, lab tests ordered for diagnosing a patient, and collected patient vitals;
receiving and storing by a database parsed HL7 data comprising the extracted specified EMR data, in real time or near real time relative to entry of the EMR data;
displaying a trackerboard by a presentation engine, wherein the trackerboard includes a graphical user interface that presents collected patient data, and wherein the collected patient data comprises:
a list of one or more patients currently admitted to an emergency department of a medical facility or hospital, wherein the list of one or more patients is determined using patient data obtained from the parsed HL7 data; and
analytic EMR data relating to one or more patients in the list of patients, wherein the analytic EMR data includes a risk assessment of emergency department (ED) visit by the one or more patients occurring within a specified time period, and is obtained from analysis of, at least, the specified EMR data relating to the one or more patients, and historical and chronologically tracked demographic and EMR data relating to information of a plurality of patients relevant to at least one particular analytical use case related to the current medical visit;
wherein the trackerboard overrides the stored parsed HL7 data in the database based on the user interaction with the graphical user interface, and
wherein the collected patient data, including the analytical EMR data, is periodically refreshed based on the parsed HL7 data and overrides received via user interaction with the trackerboard; and
overriding, by the trackerboard, the stored parsed HL7 data in the database, via user interaction with the graphical user interface, and wherein the interaction includes adding, removing, editing or updating the collected patient data.

\* \* \* \* \*